(12) United States Patent
Wang et al.

(10) Patent No.: US 7,745,598 B2
(45) Date of Patent: Jun. 29, 2010

(54) CPG SINGLE STRAND DEOXYNUCLEOTIDES FOR USE AS ADJUVANT

(75) Inventors: Liying Wang, Beijing (CN); Musheng Bao, Beijing (CN); Yongli Yu, Beijing (CN)

(73) Assignee: Changchun Huapu Biotechnology Co., Ltd., Jillin (CN)

( * ) Notice: Subject to any disclaimer, the term of this patent is extended or adjusted under 35 U.S.C. 154(b) by 0 days.

(21) Appl. No.: 12/329,398

(22) Filed: Dec. 5, 2008

(65) Prior Publication Data

US 2009/0155303 A1 Jun. 18, 2009

Related U.S. Application Data

(62) Division of application No. 11/720,070, filed as application No. PCT/CN2005/002047 on Nov. 29, 2005, now abandoned.

(30) Foreign Application Priority Data

| Nov. 29, 2004 | (CN) | ......................... 2004 1 0096082 |
| Nov. 29, 2004 | (CN) | ......................... 2004 1 0096083 |

(51) Int. Cl.
  *C07H 19/20* (2006.01)
(52) U.S. Cl. .................................................. 536/23.1
(58) Field of Classification Search ........................ None
  See application file for complete search history.

(56) References Cited

U.S. PATENT DOCUMENTS 6,406,705 B1 * 6/2002 Davis et al. .............. 424/278.1

FOREIGN PATENT DOCUMENTS

| CN | 1498895 A | 5/2004 |
| CN | 1526718 A | 9/2004 |
| CN | 1526719 A | 9/2004 |
| WO | WO 00/67023 A1 | 11/2000 |

OTHER PUBLICATIONS

Dreesen, D.W. (1997) "A Global Review of Rabies Vaccines for Human Use", *Vaccine* 15:S2-S6.

Yan J. et al. (1998) "Establishment of Rapid Fluorescence Focus Inhibition Test (RFFIT) for Detecting Neutralizing Antibody to Rabies Virus", Tsinghua Tongfang Optical Disc Co., Ltd.

* cited by examiner

*Primary Examiner*—Robert B Mondesi
*Assistant Examiner*—Nina A Archie
(74) *Attorney, Agent, or Firm*—Knobbe, Martens, Olson & Bear, LLP

(57) ABSTRACT

The present invention provides an adjuvant, which includes at least one single strand deoxynucleotide containing a CpG dinucleotide. The single strand deoxynucleotide comprises one or more CpG dinucleotides. When used in combination with rabies vaccine, HBV vaccine or other vaccines, the adjuvant can significantly improve the immune effect of the vaccine.

8 Claims, 8 Drawing Sheets

CPG SINGLE STRAND DEOXYNUCLEOTIDES FOR USE AS ADJUVANT

RELATED APPLICATIONS

This application is a divisional of application Ser. No. 11/720,070 filed Jun. 4, 2007, which is a U.S. National Phase of International Application No. PCT/CN2005/002047, filed Nov. 29, 2005, designating the U.S. and published not in English on Jun. 1, 2006 as WO 2006/056142, which claims the benefit of Chinese application No.: 200410096082.0, filed Nov. 29, 2004 and Chinese application No.: 200410096083.5, filed Nov. 29, 2004.

FIELD OF THE INVENTION

The present invention relates to a single strand deoxynucleotide containing CpG dinucleotides, and particularly relates to a single strand deoxynucleotide containing CpG dinucleotides as an adjuvant in hepatitis B virus (HBV) vaccine or rabies vaccine. The present invention further relates to sequences of the single strand deoxynucleotide containing CpG dinucleotides.

BACKGROUND OF THE INVENTION

CpG ODN is a type of oligodeoxynucleotides centered with non-methylated cytosine and guanine nucleotide (CpG). Typically, the CpG is flanked by base sequences in the following manner: 5'PurPurCGPyrPyr 3', i.e., 2 purines at its 5's end and 2 pyrimidines at its 3' end. (G Mutwiri, R. Pontarollo, S. BaBIUK. Biological activity of immunostimulatory CpG ODN motif in domestic animals. *Veterinary Immunopathology*, 2003, 91: 89-103). Studies indicate CpG ODN can activate a variety of immune effector cells, in which non-methylated CpG dinucleotides is believed to be of importance to the immunological activity of the CpG ODN. The DNAs of bacteria, viruses, and invertebrates possess immunological activation function because they have non-methylated CPG ODN sequences. The DNAs of vertebrates, in contrast, do not possess the function because their CpGs are methylated. Immune response against exogenous DNA is elicited by the immune system of the body through the recognition of the unmethylated CpG (Yi A K, Klinman D M, Martin T L, et al. Rapid immune activation by CpG motifs in bacterial DNA. Systemic induction of IL-6 transcription through an antioxidant-sensitive pathway. *Immunol.*, 1996, 157(12):5394-402).

Rabies, also referred to as hydrophobia, takes place in over 60 countries all over the world. (Wolfgang Haupt. Rabies—risk of exposure and current trends in prevention of human cases. Vaccine 1999 (17): 1742-1749). The incidence of the disease in Southeast Asia countries is higher than in other regions of the world. In mainland China, the incidence is between 0.4/100,000-1.58/100,000. Recently, the incidence of rabies grew up rapidly in many countries including China (David W Dreesen. A global review of rabies vaccines for human use. Vaccine, 1997, 15, suppl s2-s6. D. Zienius, J. Bagdonas, A. Dranseika. Epidemiological situation of rabies in Lithuania from 1990 to 2000. *Veterinary Microbiology*, 2003(93):91-100.), with a death rate of nearly 100%.

Generally, human is infected by rabies virus through for instance, animal such as dog bite, where the animal carries rabies virus. In China, 80%-90% human rabies cases are caused by infected dogs. Human rabies is an acute infectious disease characterized by the invasion of central nervous system (Alan C. Jackson, William H. Wunner. Detection of Rabies Virus Genomic RNA and mRNA in Mouse and Human Brains by Using In Situ Hybridization. *Journal of Virology*, 1991, 65(6):2839-2844.), the clinical manifestations of which include hydrophobia, anxiety, fear of wind, pharynx spasm, progressing paralysis, etc.

Rabies virus belongs to Rhabdoviridae family, with a size of about 75×180 nm. It is a single minus strand RNA encapsulated by protein capsid, the surface of which is covered by a lipoprotein envelope. The envelope further contains glycoprotein spikes. Rabies virus has immunogenicity, which can not only induce neutral antibodies but also cause RBC aggregation in animals such as chicken and goose. Rabies virus can be simply inactivated by UV radiation, quarternary ammonium compounds, iodine, potassium permanganate, alcohol, formaldehyde, etc. Heating at 100° C. for 2 minutes can also inactivate the virus. Rabies virus is tolerant to low temperatures. It can survive under −70° C. or −4° C. (in lyophilized form) for years.

Currently, there is no effective treatment for rabies infections. Up to now, rabies virus vaccine inoculation (hereafter referred to as rabies vaccine) and anti-rabies serum administration remain the major methods for preventing rabies infections. Presently in China, hamster renal cell vaccine is used as rabies vaccine. The subjects are administered 5 times intramuscularly by injection in a whole course, wherein each administration is taken on days 0, 3, 7, 14 and 30. For severe patients, they are administered 10 times in the whole course, i.e., one administration per day from the date of being bitten to 5 days after the bitten, and the rest of the administrations being taken on days 10, 14, 30 and 90. For people bitten by infected dogs, the average incidence rate is 15%-20%. In comparison, the incidence rate drops to 0.15% after taken a whole course administration.

Hepatitis B is a liver disease caused by hepatitis B virus (HBV), which has severely affected the health of people around the globe. By 2004, the number of HBV patient has reached 400,000,000 worldwide (Lin K W, Kirchner J T. Hepatitis B. *Am Fam Physician*, 2004 Jan. 1, 69(1):75-82.), most of them are Asians. In China, HBV carriers account for about 10% of the entire population. Presently, the major method to prevent HBV propagation is by way of inoculating HbsAg genetic engineering vaccine, where Aluminum is used as an adjuvant. According to WTO reports, 1 billion dosages of HBV vaccine have been consumed since 1982, which take an important role in combating the disease. The mechanism of the vaccine is that it induces the body to produce/secrete protective antibody IgG1. Although the antibody can neutralize the viruses outside of the cells, it could not thoroughly eliminate latent HBVs inside the infected cells. Furthermore, 10% of the population are low responsive or even have no response to the vaccine. Therefore, what is needed now is to improve the immunocompetence of the present HBV vaccines or to develop new vaccines which can effectively eliminate the latent HBV inside the infected cells. A number of studies on the development of novel HBV genetic engineering vaccines have been carried out from different perspectives by researchers all over the world. Among them, an important topic relates to the finding of an effective adjuvant of HBV vaccine. In recent years, CpG ODN became one of the newly discovered immunological adjuvants proved to be effective.

The result of a variety of experimental studies indicates that CpG ODN can work with HBV vaccine synergistically to induce the production of specific antibodies and elicit CTL response in murine, human, and other primates (Weeranta R D, McCluskie M J, Xu Y. et al. CpG ODN is a novel non-toxic adjuvant which induces stronger immune responses than many conventional adjuvants. *Vaccine,* 2000, 18: 1755-62.). CpG ODN is considered as a safe and effective adjuvant for HBV vaccine.

In 1988, Davis et al. immunized BALB/c mice with HBsAg and CpG ODN1826 (as adjuvant). The results of HBsAb assay indicated that the HBsAbs produced by the co-administration of HBsAg and CpG ODN as adjuvant is 5 times higher than those produced by the co-administration of HBsAg and aluminum; the HBsAbs produced by the co-administration of HBsAg, and CpG ODN as well as aluminum as adjuvants is 35 times higher than those produced by the co-administration of HBsAg and aluminum; and in control group where only HBsAg was added, no HBsAb or very low lever HBsAb was observed. All these data shows as HBsAg adjuvants, CpG ODN functions better than aluminum in inducing HBsAb production, and CpG ODN further functions synergistically with aluminum. The results of ELISA and $^{51}$Cr killing test indicated the combination use of CpG ODN and HBsAg, or the combination use of CpG ODN, aluminum and HbsAg can elicit Th1 immune response in mice, resulting in the production of IgG2a HBsAb and accompanied by HBV-specific CTL response; while the combination use of aluminum and HBsAg mainly elicited Th2 immune response in mice, resulting in the production of IgG1 HBsAb and not accompanied by HBV-specific CTL response. The in vitro antibody staining result of cell surface molecule revealed that the mechanism CpG ODN used to enhance the immunological effectiveness of HBsAg is closely associated with mechanisms through which CpG induces APC to express co-stimulative molecules, and synergistically induces the class switch of the antibodies produced by B lymphocyte (Hartmann Q Weeratna R D, Ballas Z K, et al. Delineation of a CpG phosphorothioate oligodeoxynucleotide for activating primate immune responses in vitro and in vivo. *Immunol,* 2000, 164:1617-24). All the above-discussed results suggest CpG ODN is a promising adjuvant for HBV vaccine.

SUMMARY OF THE INVENTION

In one aspect, the present invention provides a single strand deoxynucleotide containing CpG, which can be used as an adjuvant for a vaccine.

The structure of the CpG ODN according to the present invention can be represented by formulas 1-5 as follows:

The structure of the CpG ODN according to the present invention can be represented by formulas I-5 as follows:

$$(G)_n(L)_n X_1 X_2 CGY_1 Y_2(M)_n(G)_n \quad 1$$

is 0-6, $X_1$ can be adenine, thymine, guanine; $X_2$ can be adenine, thymine; $Y_1$ can be adenine, thymine; $Y_2$ can be adenine, thymine, cytosine; L and M can be adenine, thymine, guanine and cytosine;

$$(G)_n(L)_n CG(XY)_n CG(M)_n(G)_n \quad 2$$

X=A,T; Y=A,T; L,M=A,T,C,G; n is 0-6,

X can be adenine, thymine; Y can be adenine, thymine; L and M can be adenine, thymine, guanine and cytosine;

$$(TCG)_n(L)_n CG(M)_n(G)_n \quad 3$$

L,M=A,T,C,G; n is 0-6,
L,M can be adenine, thymine, guanine and cytosine;

$$(TCG)_n(L)_n X_1 X_2 CG(M)_n \quad 4$$

$X_1$ can be adenine, thymine, cytosine; $X_2$ can be adenine, thymine; L and M can be adenine, thymine, guanine and cytosine;

5. a sequence comprising TTCGTCG.

Based on the disclosure of the present invention, a skilled artisan will understand modifications can be made to the bases of the single strand deoxynucleotide, which include, but are not limited to sulpher modification, non-sulpher modification, partial sulpher modification, rare base modification (such as dI and dU), methylation modification, and other modifications where sulfhydryl, Aminolinker C6, Thiol-C6 S-S, etc. are used to couple to other substances. In addition, single strand deoxynucleotides comprising 2 or more CpG dinucleotides can function similarly to those comprising only one CpG to achieve the object of the present invention.

The single strand deoxynucleotides comprising CpG can be used in combination with other non-nucleic acid adjuvants to improve the immunological effect of a vaccine. The non-nucleic acid adjuvants include aluminum adjuvant, Freund's adjuvant, MPL, emulsions, etc.

In another aspect, the present invention provides a method for improving the immunogenicity of a vaccine, characterized by the combination use of the vaccine with the adjuvant according to the present invention, wherein the adjuvant comprises at least one single strand deoxynucleotide containing one or more CpG dinucleiotides. The vaccine includes, but is not limited to rabies vaccine and HBV vaccine. The HBV vaccine includes but is not limited to hepatitis B virus blood-derived vaccine, hepatitis B virus genetic engineering protein vaccines, hepatitis B virus transgenic plant vaccine, HBV virus vector vaccine, HBV bacterium vector vaccine and HBV DNA vaccine, of which HbsAg can be the major antigen component. Rabies vaccine includes, but is not limited to rabies virus blood-derived vaccine, rabies virus genetic engineering protein vaccines, rabies virus transgenic plant vaccine, rabies virus vector vaccine, rabies virus bacterium vector vaccine and rabies DNA vaccine. Alternatively, the adjuvant of the present invention can be used in combination with a non-nucleic acid adjuvant.

As examples, the combination use of a rabies vaccine with the adjuvant of the present invention not only significantly improved the immune response of the body to the vaccine, but also reduced the total administrations needed for the immunization; when CpG ODN is combined with HbsAg, it enhanced the immunogenicity of the HBV vaccine, quickly induced body reaction to the vaccine, elicited Th1 immune response, elongated the time limit of the immune response, reduced immune times, and improved the immunocompetence of unmatured or aged individuals. In summary, CpG ODN can be used as an effective adjuvant for HBV vaccine.

PREFERRED EMBODIMENTS FOR CARRYING OUT THE INVENTION

Figure 1:
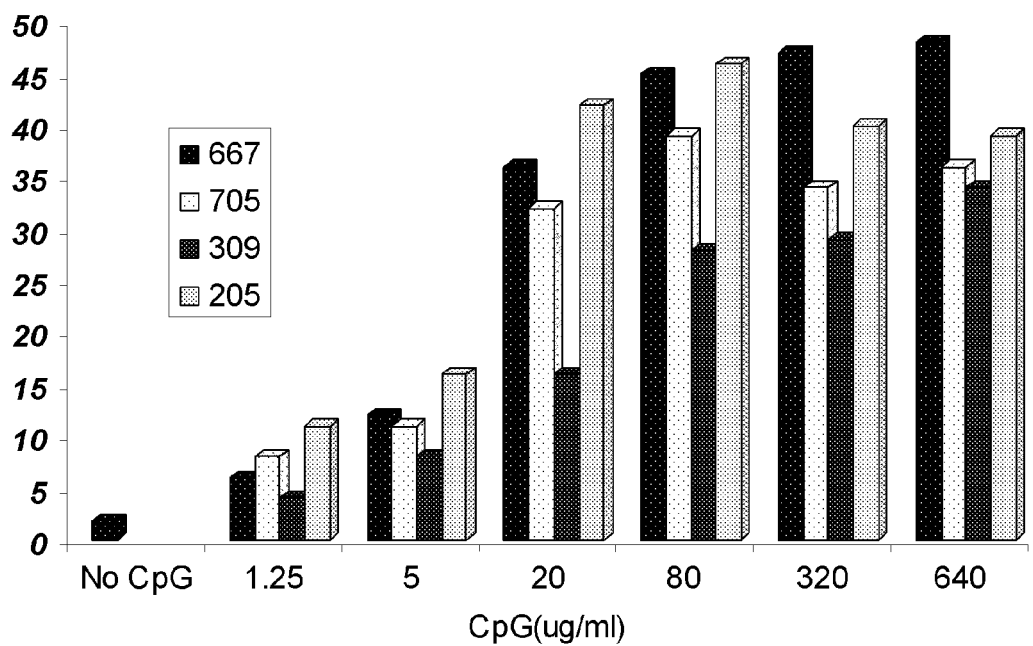
FIG. 1 shows the effects of different dosages of a CpG ODN on antibody production stimulated by rabies vaccine.

The invention will be illustrated with reference to the following examples. However, a person of ordinary skill in the art will understood the examples are included only for illustrative purposes and are not intended to limit the scope of the invention. Therefore, it is intended that this invention be limited only by the scope of the appended claims. By referring to the following examples, these and other advantages will be apparent to a skill person in the relevant art.

Example 1

Design of the Single Strand Deoxynucleotide Containing CpG

The sequences were designed as follows:

$$(G)_n(L)_n X_1 X_2 CGY_1 Y_2 (M)_n (G)_n \quad (1)$$

$X_1$=A,T,G; $X_2$=A,T; $Y_1$=A,T; $Y_2$=A,T,C; L,M=A,T,C,G; n is 0-6.

```
5'-ggggTCgTTCgTCgTTgggggg-3'      (SEQ ID NO: 1) [121]
5'-ggggATAACgTTgCggggggg-3'       (SEQ ID NO: 2) [143]
5'-ggggTgCAACgTTCAggggggg-3'      (SEQ ID NO: 3) [402]
5'-ggggTCCTACgTAggAggggggg-3'     (SEQ ID NO: 4) [123]
5'-ggggTCCATgACgTTCCTgAAggggggg-3' (SEQ ID NO: 5) [603]
5'-gggggACgTCgCCgggggggg-3'       (SEQ ID NO: 6) [118]
5'-ggATCCgTACgCATggggggg-3'       (SEQ ID NO: 7) [320]
5'-gggggAATCgATTCgggggg-3'        (SEQ ID NO: 8) [154]
5'-gggATgCATCgATgCATCggggggg-3'   (SEQ ID NO: 9) [464]
5'-ggTgCgACgTCgCAgggggg-3'        (SEQ ID NO: 10) [471]
5'-gggACgTACgTCggggggg-3'         (SEQ ID NO: 11) [390]
5'-gggggATCgACgTCgATCggggggg-3'   (SEQ ID NO: 12) [322]
5'-ggCgATCgATCgATCgggggggg-3'     (SEQ ID NO: 13) [333]
5'-ggggTCgATCgATCgAgggggg-3'      (SEQ ID NO: 14) [113]
5'-ggTCgCgATCgCgAgggggg-3'        (SEQ ID NO: 15) [307]
5'-ggGGTCAACGTTGAggggggG-3'       (SEQ ID NO: 16) [156]
5'-gTCgTTTTCgTCgACgAATTggggggg-3' (SEQ ID NO: 17) [222]
5'-gTCgTTATCgTTTTTTCgTAgggggg-3'  (SEQ ID NO: 18) [151]
5'-ggCgTTAACgACgggggg-3'          (SEQ ID NO: 19) [288]
5'-gTCggCACgCgACgggggg-3'         (SEQ ID NO: 20) [157]
5'-ggTgCgACgTCgCAgggggg-3'        (SEQ ID NO: 21) [312]
5'-gTCTATTTTgTACgTACgTgggg-3'     (SEQ ID NO: 22) [360]
5'-gACgTCgACgTCgACgTCAggggg-3'    (SEQ ID NO: 23) [209]
5'-ggggTCgATCgTTgCTAgCgggggg-3'   (SEQ ID NO: 24) [399]
5'-gggggACgTTATCgTATTggggggg-3'   (SEQ ID NO: 25) [600]
5'-ggggTCgTCgTTTgTCgTgTgTCgTTggggg-3' (SEQ ID NO: 26) [408]
5'-ACgATCgATCgATCgggggg-3'        (SEQ ID NO: 27) [304]
5'-AgACgTCTAACgTCggggg-3'         (SEQ ID NO: 28) [301]
5'-ggggTgCTggCCgTCgTTggggg-3'     (SEQ ID NO: 29) [266]
5'-ggggTCgTTgCCgTCggggggg-3'      (SEQ ID NO: 30) [248]
5'-ACCggTATCgATgCCggTgggggg-3'    (SEQ ID NO: 31) [389]
5'-TTCgTTgCATCgATgCATCgTTgggggg-3' (SEQ ID NO: 32) [287]
```

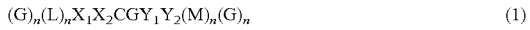

$$(G)_n(L)_n CG(XY)_n CG(M)_n (G)_n \quad (2)$$

X=A,T; Y=A,T; L,M=A,T,C,G; n is 0-6

```
5'-ggggACgATACgTCgggggggg-3'  (SEQ ID NO: 33) [546]
5'-ggggACgATATCgATgggggg-3'   (SEQ ID NO: 34) [1007]
5'-ggACgATCgATCgTggggggg-3'   (SEQ ID NO: 35) [521]
5'-TCggggACgATCgTCggggggg-3'  (SEQ ID NO: 36) [667]
5'-gggggATCgATATCgATCgggggg-3' (SEQ ID NO: 37) [576]
5'-ggATCgATCgATCgATgggggg-3'  (SEQ ID NO: 38) [268]
5'-ggTgCATCgATCgATgCAgggggg-3' (SEQ ID NO: 39) [101]
5'-ggTgCATCgTACgATgCAgggggg-3' (SEQ ID NO: 40) [100]
5'-ggTgCgATCgATCgCAgggggg-3'  (SEQ ID NO: 41) [134]
5'-gggggggTCgATCgATgggggg-3'  (SEQ ID NO: 42) [519]
5'-ggggTCgTCgAACgTTggggggg-3' (SEQ ID NO: 43) [350]
5'-TgTCgTTCCTTgTCgTT-3'       (SEQ ID NO: 44) [387]
5'-TTCgCTTCgCTTTTCgCTTCgCTT-3' (SEQ ID NO: 45) [212]
5'-ACCgCCAAggAgAAgCCgCAggAggg-3' (SEQ ID NO: 46) [166]
5'-TACAACggCgAggAATACC-3'     (SEQ ID NO: 47) [176]
5'-gTACAACggCgAggAATACCT-3'   (SEQ ID NO: 48) [523]
5'-ACCgTCgTTgCCgTCggCCC-3'    (SEQ ID NO: 49) [230]
5'-TgCTggCCgTCgTT-3'          (SEQ ID NO: 50) [435]
5'-gTCggCACgCgACg-3'          (SEQ ID NO: 51) [325]
5'-gTCggCACgCgACgCCCCCC-3'    (SEQ ID NO: 52) [523]
5'-TCCCgCTggACgTT-3'          (SEQ ID NO: 53) [188]
5'-TTACCggTTAACgTTggCCggCC-3' (SEQ ID NO: 54) [403]
5'-ACCggTTAACgTTgTCCCCgggg-3' (SEQ ID NO: 55) [420]
5'-CgTTgACgATCgTCCCATggCggg-3' (SEQ ID NO: 56) [104]
5'-TCTgCggCCTTCgTCg-3'        (SEQ ID NO: 57) [257]
5'-TAgTAACCggTCCggCgCCCCC-3'  (SEQ ID NO: 58) [221]
5'-TTgCAgCgCTgCCggTggg-3'     (SEQ ID NO: 59) [611]
5'-CggCCCATCgAgggCgACggC-3'   (SEQ ID NO: 60) [378]
5'-TCATCgACTCTCgAgCgTTC-3'    (SEQ ID NO: 61) [599]
5'-ATCgTCgACTCTCgTgTTCTC-3'   (SEQ ID NO: 62) [201]
5'-TgCAgCTTgCTgCTTgCTgCTTC-3' (SEQ ID NO: 63) [153]
5'-ggTgCgACgTCgCAgATgAT-3'    (SEQ ID NO: 64) [116]
5'-ggTCgAACgTTCgAgATgAT-3'    (SEQ ID NO: 65) [133]
5'-gggggCgTCgTTTTCgTCgACgAATT-3' (SEQ ID NO: 66) [278]
5'-actcgagacgcccgttgatagctt-3' (SEQ ID NO: 67) [244]
5'-AACgTTggCgTCgACgTCAgCgCC-3' (SEQ ID NO: 68) [623]
5'-gACgTCgACgTTgACgCT-3'      (SEQ ID NO: 69) [485]
5'-ggCgTTAACgTTAgCgCT-3'      (SEQ ID NO: 70) [579]
5'-AgCgCTAgCgCTgACgTT-3'      (SEQ ID NO: 71) [232]
5'-CTAgACgTTCAAgCgTT-3'       (SEQ ID NO: 72) [233]
5'-gACgATCgTCgACgATCgTC-3'    (SEQ ID NO: 73) [344]
5'-gTCgTTCgTAgTCgACTACgAgTT-3' (SEQ ID NO: 74) [379]
5'-AAAAgACgTCgACgTCgACgTCTTTT-3' (SEQ ID NO: 75) [489]
5'-TgCgACgATCgTCgCACgATCggAT-3' (SEQ ID NO: 76) [479]
5'-TgCgACgTCgCACAgCgT-3'      (SEQ ID NO: 77) [492]
```

$$(TCG)n(L)nCG(M)n(G)n \quad (3)$$

L,M=A,T,C,G; n is 0-6

```
5'-TCgTTgCCgTCgg-3'           (SEQ ID NO: 78) [619]
5'-TCgTTgCCgTCggg-3'          (SEQ ID NO: 79) [577]
5'-TCgTTgCCgTCgggg-3'         (SEQ ID NO: 80) [533]
5'-TCgTTgCCgTCggggg-3'        (SEQ ID NO: 81) [537]
5'-TCgTTgCCgTCgggggg-3'       (SEQ ID NO: 82) [481]
5'-TCgTTgCCgTCggggggg-3'      (SEQ ID NO: 83) [177]
```

-continued

5'-TCgTTgCCgTCgggggggg-3' (SEQ ID NO: 84) [111]

5'-TCgTTgCCgTCggggggggg-3' (SEQ ID NO: 85) [105]

5'-TCgTCgggTgCATCgATgCAgggggg-3' (SEQ ID NO: 86) [664]

5'-TCgTCgggTgCAACgTTgCAgggggg-3' (SEQ ID NO: 87) [564]

5'-TCgTCgggTgCgTCgACgCAgggggg-3' (SEQ ID NO: 88) [542]

5'-TCgTCgggTgCgATCgCAgggggg-3' (SEQ ID NO: 89) [450]

5'-TCgTCgggTgCgACgATCgTCgCAgggggg-3' (SEQ ID NO: 90) [465]

5'-TCgTCgTgCgACgTCgCAgggggg-3' (SEQ ID NO: 91) [498]

5'-TCgTCgCAgAACgTTCTggggggg-3' (SEQ ID NO: 92) [527]

5'-TCgTgCgACgTCgCAgggggg-3' (SEQ ID NO: 93) [112]

5'-TCgTgCgACgATCgTCgCAgggggg-3' (SEQ ID NO: 94) [178]

5'-TCgTATgCATCgATgCATAgggAgg-3' (SEQ ID NO: 95) [410]

5'-TCgTgCATCgATgCAgggggg-3' (SEQ ID NO: 96) [444]

5'-TCgAAACgTTTCgggggg-3' (SEQ ID NO: 97) [532]

5'-TCggACgATCgTCgggggg-3' (SEQ ID NO: 98) [598]

5'-TCgAgCgATCgCTCgAgggggg-3' (SEQ ID NO: 99) [555]

5'-TCgTCgCTTTgTCgTTgggg-3' (SEQ ID NO: 100) [418]

5'-TCgTCgTTTTgTCgTTgggg-3' (SEQ ID NO: 101) [208]

5'-TCgTCgggTgCgACgTCgCAgggggg-3' (SEQ ID NO: 102) [302]

5'-TCgTCgggTgCgACgATCgTCgggggg-3' (SEQ ID NO: 103) [290]

5'-TCgTCgTTTgCATCgATgCAgggggg-3' (SEQ ID NO: 104) [627]

5'-TCgTCgTTTTgACgATCgTCgggggg-3' (SEQ ID NO: 105) [500]

5'-TCgTTCggggTgCCg-3' (SEQ ID NO: 106) [103]

5'-TCgTTCggggTACCgATgggg-3' (SEQ ID NO: 107) [578]

5'-TCgTTgCgCTCCCATgCCgggggg-3' (SEQ ID NO: 108) [319]

5'-TCgTCgTTTCgTCgTTgggg-3' (SEQ ID NO: 109) [647]

5'-TCgTTgTCgTTTCgCTgCCggCggggg-3' (SEQ ID NO: 110) [417]

-continued

5'-TgCTTgggTggCAgCTgCCAggggggg-3' (SEQ ID NO: 111) [427]

5'-TgCTgCTTTgCTgCTTgggg-3' (SEQ ID NO: 112) [421]

5'-AACgTTCgACgTCgAACgggggggg-3' (SEQ ID NO: 113) [453]

5'-AACgACgACgTTgggggg-3' (SEQ ID NO: 114) [580]

$$(TCG)n(L)nX_1X_2CG(M)n \qquad (4)$$

$X_1$=A,T,G; $X_2$=A,T; L,M=A,T,C,G; n is 0-6

The sequences were designed as follows:

5'-TCgTAACgTTgTTTTTAACgTT-3' (SEQ ID NO: 115) [470]

5'-TCgTCgTATACgACgATCgTT-3' (SEQ ID NO: 116) [502]

5'-TCgTCgTTTgCgTTgTCgTT-3' (SEQ ID NO: 117) [601]

5'-TCCTgTCgTTTTgTCgTT-3' (SEQ ID NO: 118) [625]

5'-TCgTCgTTgTCgTTCgCT-3' (SEQ ID NO: 119) [430]

5'-TCgTCgTTACCgATgACgTCgCCgT-3' (SEQ ID NO: 120) [480]

5'-TCgTCgTTTgCATCgATgCAgTCgTCgTT-3' (SEQ ID NO: 121) [108]

5'-TCgCCTCgTCgCCTTCgAgCg-3' (SEQ ID NO: 122) [102]

5'-TCgTgTgCgTgCCgTTgggT-3' (SEQ ID NO: 123) [406]

5'-TCgTCgAgggCgCCggTgAC-3' (SEQ ID NO: 124) [560]

5'-TCgTCgCCggTgggggTgTg-3' (SEQ ID NO: 125) [629]

5'-TCgTCgTACgCAATTgTCTT-3' (SEQ ID NO: 126) [440]

5'-TCgCCCACCggTggggggggg-3' (SEQ ID NO: 127) [207]

5'-TCgTCgCAgACCggTCTgggg-3' (SEQ ID NO: 128) [615]

5'-TCgTCgCggCCggCgCCCCC-3' (SEQ ID NO: 129) [610]

5'-TCgTCgCggCCgCgAggggg-3' (SEQ ID NO: 130) [206]

5'-TCgAggACAAgATTCTCgTgC-3' (SEQ ID NO: 131) [119]

5'-TCgAggACAAgATTCTCgTgCAggCC-3' (SEQ ID NO: 132) [570]

5'-TCgTgCAggCCAACgAggCCg-3' (SEQ ID NO: 133) [631]

5'-TCgTTgCCgTCggCCC-3' (SEQ ID NO: 134) [115]

```
5'-TCggCACgCgACgTgCTggCCgTCgTTTCC-3'   (SEQ ID NO: 135) [370]
5'-TCgTTgCCgTCggCCCCCCCC-3'            (SEQ ID NO: 136) [309]
5'-TCgTTgCCgTCggCCCCCC-3'              (SEQ ID NO: 137) [506]
5'-TCgTTgCCgTCggCCCCC-3'               (SEQ ID NO: 138) [404]
5'-TCgTTgCCgTCggCCCC-3'                (SEQ ID NO: 139) [203]
5'-TCgTTgCCgTCggCCCCCCC-3'             (SEQ ID NO: 140) [501]
5'-TCgAggACAAgATTCTCgT-3'              (SEQ ID NO: 141) [305]
5'-TCggCACgCgACgTgCTggCCgTCgTT-3'      (SEQ ID NO: 142) [509]
5'-TCgTCgCgCCgTCACgggggg-3'            (SEQ ID NO: 143) [630]
5'-TCgTgTgCgTgCCgTTggg-3'              (SEQ ID NO: 144) [106]
5'-TCgTCgCCgTTgggCggg-3'               (SEQ ID NO: 145) [117]
5'-TCgTCgACgTCgTTgggCggg-3'            (SEQ ID NO: 146) [280]
5'-TCgCAgTTgTCgTAACgTTgggCggg-3'       (SEQ ID NO: 147) [205]
5'-TCgTCgTTggTATgTT-3'                 (SEQ ID NO: 148) [613]
5'-TCgTCgTCgTCgTTgTCgTT-3'             (SEQ ID NO: 149) [306]
5'-TCgTCgTCgTCgTTgTCgTTgggg-3'         (SEQ ID NO: 150) [640]
5'-TCgTTCggggTgCCg-3'                  (SEQ ID NO: 151) [409]
5'-TCgTTCggggTAACgATT-3'               (SEQ ID NO: 152) [508]
5'-TCgTTCggggTAACgTT-3'                (SEQ ID NO: 153) [540]
5'-TCgTTCggggTACCgAT-3'                (SEQ ID NO: 154) [401]
5'-TCgTACggCCgCCgTACggCggg-3'          (SEQ ID NO: 155) [607]
5'-TCgCgTCgACTCCCCTCgAgggg-3'          (SEQ ID NO: 156) [380]
5'-TCgTCgTCgACTCgTggTCgggg-3'          (SEQ ID NO: 157) [656]
5'-TCgggCgCCCgATCgggggg-3'             (SEQ ID NO: 158) [310]
5'-TCgTCggTCTTTCgAAATT-3'              (SEQ ID NO: 159) [109]
5'-TCgTgACgTCCTCgAgTT-3'               (SEQ ID NO: 160) [330]
5'-TCgTCTTTCgACTCgTTCTC-3'             (SEQ ID NO: 161) [605]
5'-TCgTCgTTTTgCgTTCTC-3'               (SEQ ID NO: 162) [504]
5'-TCgACTTTCgTCgTTCTgTT-3'             (SEQ ID NO: 163) [407]
5'-TCgTCgTTTCgTCgTTCTC-3'              (SEQ ID NO: 164) [550]
5'-TCgTCgTCgTCgTTgTCgTT-3'             (SEQ ID NO: 165) [612]
5'-TCgTTCTCgACTCgTTCTC-3'              (SEQ ID NO: 166) [277]
5'-TCgACgTTCgTCgTTCgTCgTTC-3'          (SEQ ID NO: 167) [684]
5'-TCgTCgACgTCgTTCgTTCTC-3'            (SEQ ID NO: 168) [685]
5'-TCgTgCgACgTCgCAgATgAT-3'            (SEQ ID NO: 169) [114]
5'-TCgTCgAgCgCTCgATCggAT-3'            (SEQ ID NO: 170) [211]
5'-TCgTCgTTTCgTAgTCgTTgACgTCggg-3'     (SEQ ID NO: 171) [204]
5'-TCgTCggACgTTTTCCgACgTTCT-3'         (SEQ ID NO: 172) [308]
5'-TCgTCgTTTTCgTCgTTTTCgTCgTT-3'       (SEQ ID NO: 173) [340]
5'-TCgTCgTTTgTCgTgTgTCgTT-3'           (SEQ ID NO: 174) [503]
5'-TCgTCgTTggTCggggTCgTTggggTCgTT-3'   (SEQ ID NO: 175) [405]
5'-TCgTCgTTTCgTCTCTCgTT-3'             (SEQ ID NO: 176) [614]
5'-TCgTCgTTTTgCTgCgTCgTT-3'            (SEQ ID NO: 177) [505]
5'-TCgAgCgTTTTCgCTCgAATT-3'            (SEQ ID NO: 178) [530]
```

(5) Sequences Containing TTCGTCG

```
5'-TTCgTCgTTTgATCgATgTTCgTTgggggg-3'   (SEQ ID NO: 179) [507]
5'-TTCgTCgTTgTgATCgATgggggg-3'         (SEQ ID NO: 180) [210]
5'-TATCgATgTTTTCgTCgTCgTTgggggg-3'     (SEQ ID NO: 181) [202]
5'-TCgACTTTCgTCgTTCTgTT-3'             (SEQ ID NO: 182) [303]
5'-TCgTCgTTTCgTCgTTCTC-3'              (SEQ ID NO: 183) [491]
5'-TCgACgTTCgTCgTTCgTCgTTC-3'          (SEQ ID NO: 184) [590]
5'-TCgTCgTTTTCgTCgTTTTCgTCgTT-3'       (SEQ ID NO: 185) [633]
```

Preferably, CpG ODNs according to the present invention have the following sequences:

```
                                                    (SEQ ID NO: 109)
CpG[647]/[205]:  5'-TCgTCgTTTCgTCgTTgggg-3'

(SEQ ID NO: 150)
CpG[640]/[309]:  5'-TCgTCgTCgTCgTTgTCgTTgggg-3'

(SEQ ID NO: 167)
CpG[684]/[667]:  5'-TCgACgTTCgTCgTTCgTCgTTC-3'

(SEQ ID NO: 168)
CpG[685]/[705]:  5'-TCgTCgACgTCgTTCgTTCTC-3'
```

In the following examples, CpG ODN sequences will be represented by the numbers in above brackets.

Example 2

Synthesis of the Single Strand Deoxynucleotide Containing CpG

DNA fragment was synthesized by solid phasephosphoramidite triester method. The method has been widely used in chemical synthesis of DNA due to its advantages of fast, high efficiency, etc.

Chemical synthesis of DNA is different from enzymatic synthesis of DNA. The latter is synthesized from 5' end to 3' end, while the former starts from 3' end. The synthesis steps are as follows:

1. De-Protection

Trichloroacetic acid was used to remove protective group DMT conjugated to the nucleotides on Controlled Pore Glass (CPG) to obtain free 5' hydroxyl ends for being used in the following condensation reaction.

2. Activation

The nucleotides units protected by phosphoramidite was mixed with tetrazolium activator and then loaded into a synthesis column to form an active intermediate of phosphoramiditetetrazole (the 3' end of which is activated, while the 5' end of which is still under DMT protection). The intermediate then reacted with the de-protected nucleotide on CPG in a condensation reaction.

3. Linking

When contacted with the de-protected nucleotide on CPQ the intermediate reacted with its 5' hydroxyl group, and released tetrazole group in the condensation reaction. In such a way, one base was added to the synthesized oligonucleotide strand.

4. Blocking

After the condensation reaction, acetylation is commonly used to block the hydroxyl end to prevent unreacted 5'hydroxyl group conjugated on CPG from further being extended in the following reactions. Generally, reactants used in acetylation are formulated by mixing acetic anhydride, N-methylimidazole, and the like.

5. Oxidation

In the condensation reaction, a nucleotide bonded with the oligonucleotide on CPG through phosphate bond. Since phosphate bond is unstable, easy to be hydrolyzed by acids or bases, the tetrahydrofuran solution of iodine is conventionally used to transform phosphoramidite into phosphoric triester to produce stable oligonucleotides.

Through the five steps described above, a deoxynucleotide was bonded to the nucleotides on CPG Likewise, after repeating all these five steps, a crude DNA fragment was obtained. The fragment was then subjected to post-synthesis processing such as cleavage, de-protection (generally, benzoyl protection is used for bases A and C; isobutyryl protection is used for base G; no protection is needed for base T; nitrile ethyl protection is used for phosphorous acid), purification (conventional methods such as HAP, PAGE, HPLC, C18, and OPC etc.) and quantification to produce oligonucleotide fragments qualified for experimental use.

Solid-phase oligonucleotide synthesis was carried out on a DNA synthesizer. After the protective groups were removed, the purity of the interest oligonucleotides produced by the method described above was very low, containing a large amount of impurities. Major impurities include benzoic acid ammonia and isobutyric acid ammonia formed by the removed protective groups and ammonia, nitrile ethyl from nitrile phosphate, and short chains produced during the synthesis. As a result, the content of the oligonucleotide in the crude product is only about 15%. Though the efficiency in every synthesis step is around 97%-98%, the add-up efficiency of the whole process is not high. As such, the content of the oligonucleotide of interest can not even reach 10%. Impurities such as salts and short chains in the crude product not only make the quantification inaccurate, but also influence the next reactions. Therefore, the oligonucleotides must be further purified. Polyacrylamide gel electrophoresis (PAGE) method is preferably used for the purification. The method can be conveniently used in most molecular biology laboratories and the products purified by the method can achieve relatively high purity. When cost becomes an issue, desalination can be used for some experiments with relatively lower requirements such as PCR.

Oligonucleotide fragment is quantified by $OD_{260}$ value. In 1 ml standard quartz cuvette with a light path of 1 cm, a oligonucleotide solution with an absorbance of 1 under 260 nm wavelength is defined as 1 $OD_{260}$. Although the bases makeup in each specific oligonucleotide are not exactly the same, the weight of a oligonucleotide of 1 $OD_{260}$ is about 33 μg.

Example 3

Effects of Different Dosages of a CpG ODN on Antibody Production Stimulated by Rabies Vaccine 1 Experimental animals: 200 white mice, with half males and half females, weighted from 18 to 22 g, aged from 6 to 8 weeks, and purchased from Beijing Weitonglihua Experimental Animal Ltd.

2. Rabies vaccine: 1 ml/vial (containing 2.5 IU), purchased from Changchun Institute of Biological Product.

3 CpGODN: synthesized by Shanghai Shenggong Biotechnology Service Ltd.

4. Experimental groups: 8 mice for each group, with half males and half females.

rabies vaccine
rabies vaccine+1.25 μg CpG667
rabies vaccine+1.25 μg CpG705
rabies vaccine+1.25 μg CpG309
rabies vaccine+1.25 μg CpG205
rabies vaccine+5 μg CpG667
rabies vaccine+5 μg CpG705
rabies vaccine+5 μg CpG309
rabies vaccine+5 μg CpG205
rabies vaccine+20 μg CpG667
rabies vaccine+20 μg CpG705
rabies vaccine+20 μg CpG309
rabies vaccine+20 μg CpG205
rabies vaccine+80 μg CpG667 rabies vaccine+80 μg CpG705
rabies vaccine+80 μg CpG309
rabies vaccine+80 μg CpG205
rabies vaccine+320 μg CpG667
rabies vaccine+320 μg CpG705
rabies vaccine+320 μg CpG309
rabies vaccine+320 μg CpG205
rabies vaccine+640 μg CpG667
rabies vaccine+640 μg CpG705
rabies vaccine+640 μg CpG309
rabies vaccine+640 μg CpG205

5. CpGODN formulation: 50 μl PBS was used to dissolve different dosages of CpGODN to prepare CpGODN solutions with different concentrations.

6. White mice inoculation: On days 0, 3, 7, 14 and 28, rabies vaccine or rabies vaccine+CpG ODN as listed above in experimental groups were respectively administrated to white mice via intraperitoneal injection, wherein the dosage of rabies vaccine is 0.5 ml/mouse.

7. Experimental groups: 8 mice for each group, with half males and half females.

A volume of 0.5 ml was used in the inoculation.

8. Rabies vaccine antibody assay: On day 35, blood was drawn from the caudal vein of the white mice. The blood was assayed with Quick Rabies vaccine Fluorescence Foci Inhibitory test (RFFIT) (Yan jiaxin, Li chengping, Zhu jiahong, et al. The establishment of a quick rabies vaccine fluorescence foci inhibitory experimental method to detect the neutral antibody of rabies virus. *Journal of China Biological Product,* 1998, 11 (2): 93-96; Ministry of Health of PRC. Chinese Biological Product Regulations (Department 1), Beijing: Chinese Population Publishing House, 1996, 201.) to detect rabies virus-specific antibodies in serum. The blood was drawn from caudal vein of the mice two days prior to the inoculation, and the serum obtained was used as negative control.

9. Results: With the increase of the dosage of CpG ODN, the level of rabies vaccine-specific antibodies in mice sera also increased (See FIG. 1).

10. Conclusion: CpG ODN can significantly improve the production of rabies vaccine-specific antibodies in white mice elicited by rabies vaccine, which indicates CpG ODN can be used as an effective adjuvant for a rabies vaccine.

Example 4

Effects of the Combination Use of Aluminum Adjuvant and Different Dosages of a CpG ODN on Antibody Production Stimulated by Rabies Vaccine 1 Experimental animals: 200 white mice, with half males and half females, weighted from 18 to 22 g, aged from 6 to 8 weeks, and purchased from Beijing Weitonglihua Experimental Animal Ltd.

2. Rabies vaccine: 1 ml/vial (containing 2.5IU), purchased from Changchun Institute of Biological Product.

3 CpGODN: synthesized by Shanghai Shenggong Biotechnology Service Ltd.

4. Experimental groups: 8 mice for each group, with half males and half females.
  rabies vaccine
  rabies vaccine+Al adjuvant (purchased from Changchun Institute of Biological Product)
    rabies vaccine+1.25 μg CpG667+Al adjuvant
    rabies vaccine+1.25 μg CpG705+Al adjuvant
    rabies vaccine+1.25 μg CpG309+Al adjuvant
    rabies vaccine+1.25 μg CpG205+Al adjuvant
    rabies vaccine+5 μg CpG667+Al adjuvant
    rabies vaccine+5 μg CpG705+Al adjuvant
    rabies vaccine+5 μg CpG309+Al adjuvant
    rabies vaccine+5 μg CpG205+Al adjuvant
    rabies vaccine+20 μg CpG667+Al adjuvant
    rabies vaccine+20 μg CpG705+Al adjuvant
    rabies vaccine+20 μg CpG309+Al adjuvant
    rabies vaccine+20 μg CpG205+Al adjuvant
    rabies vaccine+80 μg CpG667+Al adjuvant
    rabies vaccine+80 μg CpG705+Al adjuvant
    rabies vaccine+80 μg CpG309+Al adjuvant
    rabies vaccine+80 μg CpG205+Al adjuvant
    rabies vaccine+320 μg CpG667+Al adjuvant
    rabies vaccine+320 μg CpG705+Al adjuvant
    rabies vaccine+320 μg CpG309+Al adjuvant
    rabies vaccine+320 μg CpG205+Al adjuvant
    rabies vaccine+640 μg CpG667+Al adjuvant
    rabies vaccine+640 μg CpG705+Al adjuvant
    rabies vaccine+640 μg CpG309+Al adjuvant
    rabies vaccine+640 μg CpG205+Al adjuvant 5. CpGODN formulation: 50 μl PBS was used to dissolve different dosages of a CpGODN to prepare CpGODN solutions with different concentrations.

6. White mice inoculation: On days 0, 3, 7, 14 and 28, rabies vaccine+Al adjuvant or rabies vaccine+Al adjuvant+CpG ODN as listed above in experimental groups were respectively administrated to white mice via intraperitoneal injection. The dosage of rabies vaccine used is 0.5 ml, and the final concentration of the Al adjuvant is 0.5 mg/ml.

7. Rabies vaccine antibody assay: On day 35, blood was drawn from the caudal vein of the white mice. The serum was assayed with Quick Rabies vaccine Fluorescence Foci Inhibitory test (RFFIT) to detect the titers of rabies virus-specific antibodies in serum. The blood was drawn from caudal vein of the mice two days prior to the inoculation, and the serum obtained was used as negative control.

Figure 2:
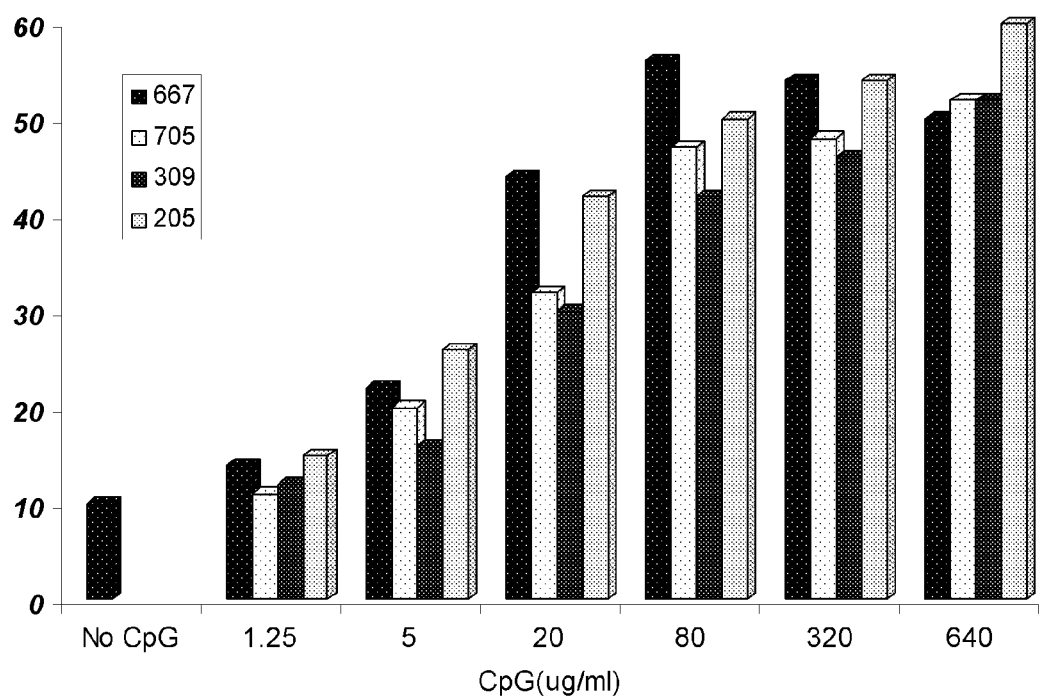
FIG. 2 shows the effects of the combination use of aluminum adjuvant and different dosages of a CpG ODN on antibody production stimulated by rabies vaccine.

8. Results: With the increase of the dosage of CpG ODN, the level of rabies vaccine-specific antibodies in mice sera also increased. FIG. 2 shows the effects of the combination use of aluminum adjuvant and different dosages of CPG ODN on antibody production stimulated by rabies vaccine.

9. Conclusion: CpG ODN and Al adjuvant can significantly improve the production of rabies vaccine-specific antibodies in white mice elicited by rabies vaccine, which indicates the combination of CpG ODN and Al can be used effectively as a potent adjuvant for a rabies vaccine.

Example 5

Effect of CPG ODN on the Speed of Antibody Production Stimulated by Rabies Vaccine 1. Experimental animals: 80 white mice, with half males and half females, weighted from 18 to 22 g, aged from 6 to 8 weeks, and purchased from Beijing Weitonglihua Experimental Animal Ltd.

2. Rabies vaccine: 1 ml/vial (containing 2.5 IU), purchased from Changchun Institute of Biological Product.

3. CpGODN: synthesized by Shanghai Shenggong Biotechnology Service Ltd.

4. Experimental groups: 8 mice for each group, with half males and half females.
  rabies vaccine
  rabies vaccine+Al adjuvant
  rabies vaccine+80 μg CpG667
  rabies vaccine+80 μg CpG667+Al adjuvant
  rabies vaccine+80 μg CpG705 rabies vaccine+80 µg CpG705+Al adjuvant
rabies vaccine+80 µg CpG309
rabies vaccine+80 µg CpG309+Al adjuvant
rabies vaccine+80 µg CpG205
rabies vaccine+80 µg CpG205+Al adjuvant All the above rabies vaccines and CpGODNs were dissolved in PBS.

5. White mice inoculation: On days 0, 3, 7, 14 and 28, rabies vaccine or rabies vaccine+Al adjuvant or rabies vaccine+Al adjuvant+CpG ODN as listed above in experimental groups were respectively administrated to white mice via intraperitoneal injection. The dosage of rabies vaccine used is 0.5 ml/mouse, and the final concentration of the Al adjuvant is 0.5 mg/ml.

6 Rabies vaccine antibody assay: On days 0, 5, 7, 14, 28, 35, 49, 63, and 77, blood was drawn from the caudal vein of the white mice, and the serum was separated from the blood. The serum was assayed with Quick Rabies vaccine Fluorescence Foci Inhibitory test (RFFIT) to evaluate the titers of the rabies vaccine antibodies produced. The blood was drawn from caudal vein of the mice two days prior to the inoculation, and the serum obtained was used as negative control.

Figure 3:
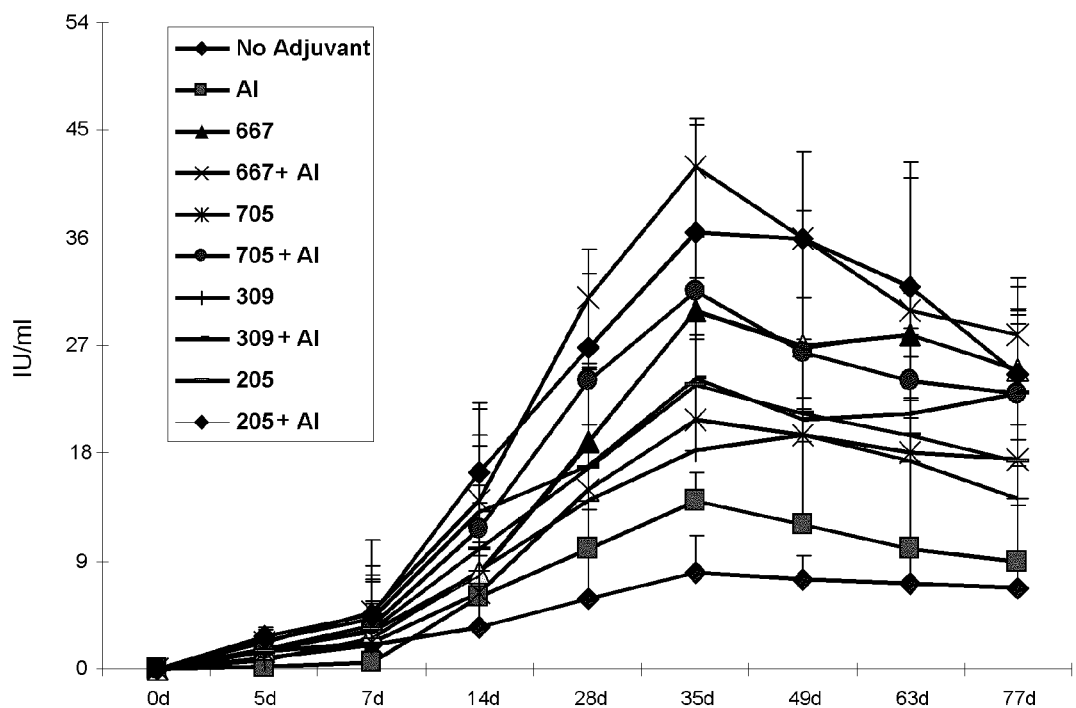
FIG. 3 shows the effect of CpG ODN on the speed of antibody production stimulated by rabies vaccine.

7. Results: When CpGODN and Al adjuvant were used in combination, the titer of the antibodies produced at any specific time was higher than those of the antibodies produced where rabies vaccine, Al adjuvant, or CpG ODN was used alone (See FIG. 3).

8. Conclusion: The combination use of CpG ODN and Al adjuvant can expediate the appearance of the rabies virus-specific antibody in mice immunized with rabies vaccine.

Example 6

Evaluation of Whether CpG ODN, as an Adjuvant for a Rabies Vaccine, Can Reduce the Immune Times Needed for a Rabies Vaccination 1. Experimental animals: 80 white mice, with half males and half females, weighted from 18 to 22 g, aged from 6 to 8 weeks, and purchased from Beijing Weitonglihua Experimental Animal Ltd.

2. Rabies vaccine: 1 ml/vial (containing 2.5 IU), purchased from Changchun Institute of Biological Product.

3. CpGODN: synthesized by Shanghai Shenggong Biotechnology Service Ltd.

4. Experimental groups: a total of 10 groups, with 8 mice for each group, half males and half females.
rabies vaccine
rabies vaccine+Al adjuvant
rabies vaccine+80 µg CpG667
rabies vaccine+80 µg CpG667+Al adjuvant
rabies vaccine+80 µg CpG705
rabies vaccine+80 µg CpG705+Al adjuvant
rabies vaccine+80 µg CpG309
rabies vaccine+80 µg CpG309+Al adjuvant
rabies vaccine+80 µg CpG205
rabies vaccine+80 µg CpG205+Al adjuvant All the above rabies vaccines and CpGODNs were dissolved in PBS.

5. Immunization: The mice were immunized according to different groups. 0.5 ml of rabies vaccine was used to inoculate the mice via intraperitoneal injection. The immune times were set to 5, 4, and 3. When the immune times was set to 5, the mice was inoculated on days 0, 3, 7, 14, and 28, respectively. When the immune times was set to 4, the mice was inoculated on days 0, 7, 14, and 28, respectively. When the immune times was set to 3, the mice was inoculated on days 0, 7, and 21, respectively. Rabies vaccine or rabies vaccine+Al adjuvant or rabies vaccine+Al adjuvant+CpG ODN as listed above in different group were respectively administrated to white mice via intraperitoneal injection. The final concentration of the Al adjuvant is 0.5 mg/ml.

6. Rabies vaccine antibody assay: Blood was drawn from the caudal vein of the white mice, and the serum was separated from the blood 7 days after the final inoculation. The serum was assayed with Quick Rabies vaccine Fluorescence Foci Inhibitory test (RFFIT) to test the titers of the rabies vaccine antibodies produced. The blood was drawn from caudal vein of the mice two days prior to the inoculation, and the serum obtained was used as negative control.

Figure 4:
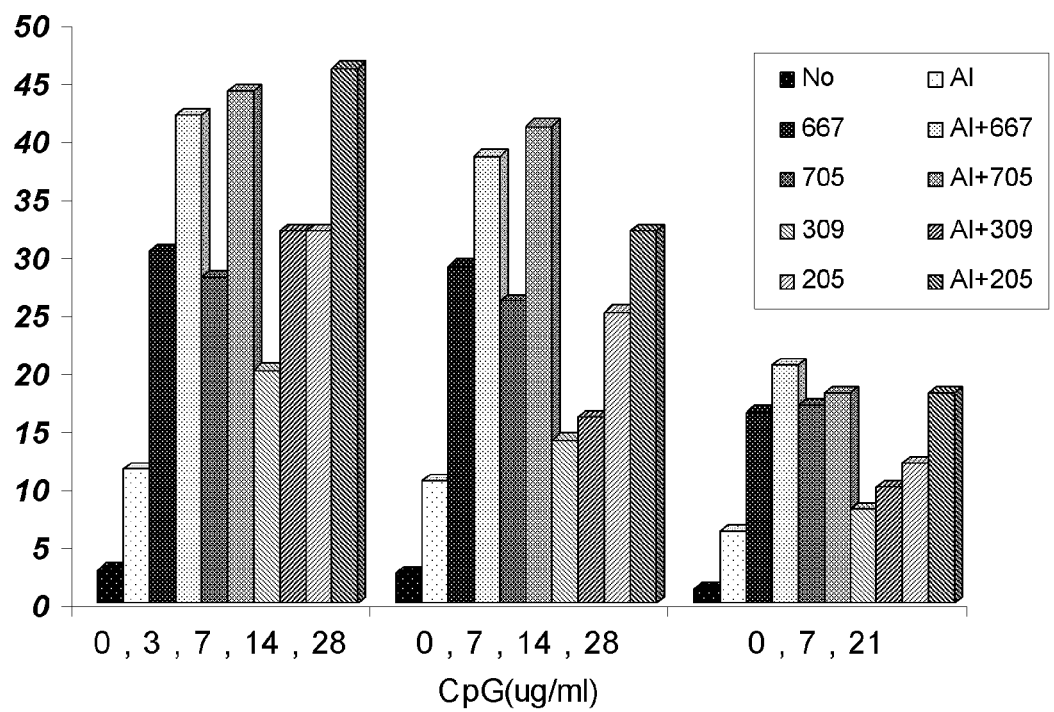
FIG. 4 shows the evaluation of whether CpG ODN, as an adjuvant, can reduce the immune times needed for the rabies vaccination.

7. Results: The combination use of CpGODN and Al adjuvant can produce relatively high levels of rabies virus-specific antibodies in mice immunized with rabies vaccine by 3, 4 or 5 times (See FIG. 4).

8. Conclusion: The combination use of CpGODN and Al adjuvant can produce a relatively high level of rabies virus-specific antibodies in mice immunized with rabies vaccine by 3 times.

Example 7

Evaluation of Whether CpG ODN, as an Adjuvant for a Rabies Vaccine, Can Reduce the Dosages Needed for the Rabies Vaccination 1. Experimental animals: 128 white mice, with half males and half females, weighted from 18 to 22 g, aged from 6 to 8 weeks, and purchased from Beijing Weitonglihua Experimental Animal Ltd.

2. Rabies vaccine: 1 ml/vial (containing 2.5 IU), purchased from Changchun Institute of Biological Product.

3. CpGODN: synthesized by Shanghai Shenggong Biotechnology Service Ltd.

4. Experimental groups: 8 mice for each group, with half males and half females.
rabies vaccine+80 µg CpG705+Al adjuvant
½ rabies vaccine+80 µg CpG705+Al adjuvant
¼ rabies vaccine+80 µg CpG705+Al adjuvant
⅛ rabies vaccine+80 µg CpG705+Al adjuvant
rabies vaccine+80 µg CpG667+Al adjuvant
½ rabies vaccine+80 µg CpG667+Al adjuvant
¼ rabies vaccine+80 µg CpG667+Al adjuvant
⅛ rabies vaccine+80 µg CpG667+Al adjuvant
rabies vaccine+80 µg CpG309+Al adjuvant
½ rabies vaccine+80 µg CpG309+Al adjuvant
¼ rabies vaccine+80 µg CpG309+Al adjuvant
⅛ rabies vaccine+80 µg CpG309+Al adjuvant
rabies vaccine+80 µg CpG205+Al adjuvant
½ rabies vaccine+80 µg CpG205+Al adjuvant
¼ rabies vaccine+80 µg CpG205+Al adjuvant
⅛ rabies vaccine+80 µg CpG205+Al adjuvant All the above rabies vaccines and CpGODNs were dissolved in PBS.

5. White mice inoculation: On days 0, 3, 7, 14 and 21, white mice were immunized according to different groups. 0.5 ml/mouse of rabies vaccine was inoculated to the mice via intraperitoneal injection. The final concentration of the Al adjuvant is 0.5 mg/ml.

6. Rabies vaccine antibody assay: On day 28, blood was drawn from the caudal vein of the white mice, and the serum was separated from the blood. The serum was assayed with Quick Rabies vaccine Fluorescence Foci Inhibitory test (RFFIT) to evaluate the titers of the rabies vaccine antibodies produced. The blood was drawn from caudal vein of the mice two days prior to the inoculation, and the serum obtained was used as negative control.

Figure 5:
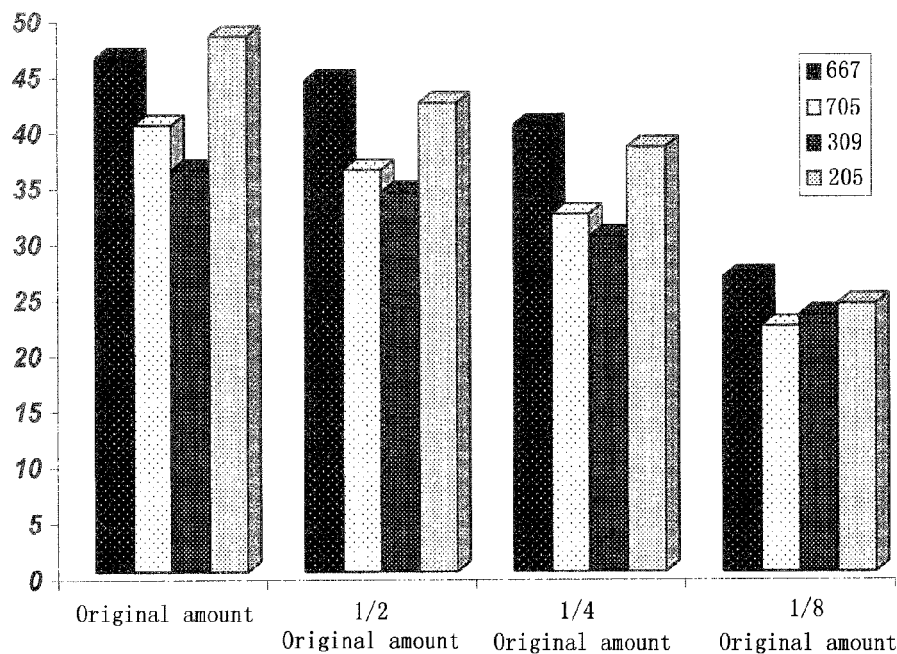
FIG. 5 shows the evaluation of whether CpG ODN, as an adjuvant, can reduce the dosages needed for the rabies vaccination.

7. Results: The combination use of CpG and reduced amount of rabies vaccine can still elicit a relatively high level of rabies virus-specific antibody production, indicating CpG ODN can lower the dosage of the rabies vaccine (See FIG. 5).

8. Conclusion: CpG ODN can lower the dosage of the rabies vaccine.

Example 8

Effects of Different CpG ODNs on Antibody Production Stimulated by Rabies Vaccine 1. Experimental animals: 112 white mice, with half males and half females, weighted from 18 to 22 g, aged from 6 to 8 weeks, and purchased from Beijing Weitonglihua Experimental Animal Ltd.

2. Rabies vaccine: 1 ml/vial (containing 2.5 IU), purchased from Changchun Institute of Biological Product.

3. CpGODN: synthesized by Shanghai Shenggong Biotechnology Service Ltd.

4. Control sequence:
5'-TCgTCgTTTTgTCgTTTTgTcgTT-3'[2006]

5. Experimental groups: 8 mice for each group, with half males and half females.

rabies vaccine
rabies vaccine+Al adjuvant
rabies vaccine+80 μg CpG667
rabies vaccine+80 μg CpG667+Al adjuvant
rabies vaccine+80 μg CpG705
rabies vaccine+80 μg CpG705+Al adjuvant
rabies vaccine+80 μg CpG309
rabies vaccine+80 μg CpG309+Al adjuvant
rabies vaccine+80 μg CpG205
rabies vaccine+80 μg CpG205+Al adjuvant
rabies vaccine+80 μg CpG607
rabies vaccine+80 μg CpG607+Al adjuvant
rabies vaccine+80 μg CpG2006
rabies vaccine+80 μg CpG2006+Al adjuvant All the above rabies vaccine and CpG ODN were dissolved in PBS.

6. White mice inoculation: On days 0, 3, 7, 14 and 21, white mice were immunized according to different groups. 0.5 ml/mouse of rabies vaccine was inoculated to the mice via intraperitoneal injection. The final concentration of the Al adjuvant is 0.5 mg/ml.

7. Rabies vaccine antibody assay: On day 35, blood was drawn from the caudal vein of the white mice, and the serum was separated from the blood. The serum was assayed with Quick Rabies vaccine Fluorescence Foci Inhibitory test (RF-FIT) to detect the titers of rabies virus-specific antibodies in serum. The blood was drawn from caudal vein of the mice two days prior to the inoculation, and the serum obtained was used as negative control.

Figure 6:
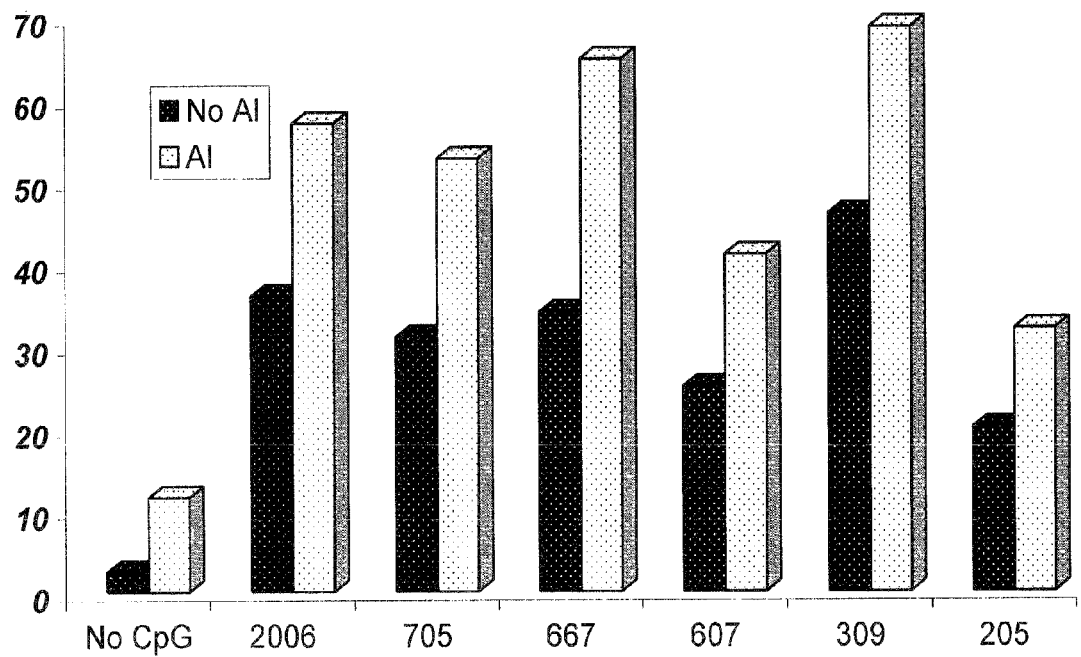
FIG. 6 shows the effects of different CpG ODNs on antibody production stimulated by rabies vaccine.

8. Results: The effect of antibody production elicited by rabies vaccine+CpG667 or rabies vaccine+CpG309 is significantly superior to that elicited by rabies vaccine+CpG2006 (See FIG. 6).

9. Conclusion: CpGODN667 and CpGODN309 can significantly improve the immune effect of rabies vaccine.

Example 9

HBV Antibody Assay by ELISA

I. Regents

1. HBsAg (containing no Al adjuvant, Beijing Institute of Biological Product) vaccine formulation: 1 mg lyophilized HBsAg protein powder was dissolved into 1 ml PBS to prepare stock solution (1 mg/ml).

2. HRP-Horse-anti-mouse secondary antibody: Beijing Dingguo Biotechnology Ltd.

3. PBS: 1000 ml

| NaCl | 8 g (Beijing Chemical Plant) |
|---|---|
| KCl | 0.2 g (Beijing Chemical Plant) |
| $Na_2HPO_4 \cdot 12H_2O$ | 2.9 g (Beijing Chemical Plant) |
| $KH_2PO4$ | 0.2 g (Beijing Chemical Plant) |

After dissolved in 800 ml ultra pure water, the pH of the resultant solution was adjusted to 7.2-7.4 by HCl or NaOH, and then made up to a volume of 1000 ml.

4. Coating solution: 100 ml

| PBS | 80 ml |
|---|---|
| 50% glutaraldehyde | 1.6 ml (Beijing Chemical Plant) |

After sufficiently dissolved, the resultant solution was made up to a volume of 100 ml with PBS.

5. Washing solution: 500 ml

| PBS | 400 ml |
|---|---|
| Tween20 | 0.5 ml (Beijing Chemical Plant) |
| NaCl | 14.625 g (Beijing Chemical Plant) |

After sufficiently dissolved, the resultant solution was made up to a volume of 500 ml with PBS.

6. Blocking solution 100 ml

| PBS | 80 ml |
|---|---|
| Skimmed milk | 5 g (Beijing Dingguo Biotechnology Ltd.) |
| BSA | 1 g (Beijing Dingguo Biotechnology Ltd.) |

After sufficiently dissolved, the solution was made up to a volume of 100 ml with PBS, followed by adding 0.05 g of sodium azide.

7. Sample diluent 1000 ml

| Tris | 2.42 g (Beijing Chemical Plant) |
|---|---|
| NaCl | 8.77 g (Beijing Chemical Plant) |

After dissolved in 800 ml ultra pure water, the pH of the resultant solution was adjusted to 7.1 with HCl, followed by the addition of

| BSA | 1 g |
|---|---|
| Tween20 | 0.5 ml | ultra pure water was used to make up the solution to a volume of 1000 ml.

8. Substrate solution:
Solution A:

| citric acid | 19.2 g (Beijing Chemical Plant) |

After dissolved in 800 ml ultra pure water, the resultant solution was made up to a volume of 1000 ml with the ultra pure water.
Solution B:

| $Na_2HPO_4 \cdot 12H_2O$ | 71.7 g (Beijing Chemical Plant) |

After dissolved in 800 ml ultra pure water, the resultant solution was made up to a volume of 1000 ml with the ultra pure water.
Substrate Solution:

| Solution A | 47.276 ml |
| Solution B | 50 ml |

Above volumes of Solution A and Solution B were taken respectively and mixed, followed by filtration through a 0.22 μm filter to remove bacteria.
9. Stop solution: 100 ml

| Concentrated $H_2SO_4$ | 20 ml (Beijing Chemical Plant) | slowly added into 80 ml ultra pure water while stirring.

II. Methods
1. Coating: 100 μl HBsAg (1 mg/ml) was added into 10 ml coating solution, i.e., the HBsAg was diluted to a final concentration of 10 μg/ml by the coating solution. Then, 100 μl diluted HBsAg was added into each well of an ELISA plate, which was then left stand overnight under a temperature of 4° C.
2. Washing: The next day, the liquid left in the wells of the plate was removed completely, and 300 μl washing solution was added into each well. Before removing the washing solution, the plate was left stand for 3 minute at room temperature. Finally, the plate was dried by tapping on an absorbent paper. Same washing procedure was repeated for 3 times.
3. Blocking: 300 μl blocking solution was added into the wells of the ELISA plate, and was left stand for 2 hs at room temperature.
4. Adding samples to be tested: Same washing procedures described in step 2 were applied. Samples to be tested were diluted with sample diluent into different concentrations before being added. 100 μl/well diluted sample was added into wells in duplicate and was left stand for 2 hs at room temperature.
5. Adding HRP-horse-anti-mouse secondary antibody: Same washing procedures described in step 2 were applied. IRP-horse-anti-mouse secondary antibody was diluted with sample diluent (1:1000). 100 μl/well diluted IRP-horse-anti-mouse secondary antibody was added into wells and was left stand for 2 hs in darkness at room temperature.
6. Adding substrate solution: Same washing procedures described in step 2 were applied. 100 μl freshly made substrate solution was added into each well, and left stand for 20 minutes in darkness at room temperature.
7. Adding stop solution: The ELISA plate was incubated for 20 minutes, after which 50 μl stop solution was added into each well.
8. ELISA assay (A492 nm): ELISA assay (A492 nm) was carried out within 5 minutes after the addition of the stop solution.
9. Determination of a positive value: A positive value is defined where the OD value of a sample/the OD value of the negative control is 2 or more.

Example 10

Comparison of the Effects of Different CpG ODNs on Antibody Production Stimulated by HBsAg I. Animals and Regents
1. Animals: BALB/c mouse, female, aged from 6-8 weeks (available from Beijing Weitonglihua Experimental Animal Ltd.).
2. HBsAg: containing no Al adjuvant, purchased from Changchun Institute of Biological Product.
3. CpGODN: synthesized by Shanghai Shenggong Biotechnology Service Ltd.
4. CpGODN formulation: 100 μg CpG ODN was dissolved into 50 μl PBS to prepare application solution.
5. HBsAg formulation: 1 mg lyophilized HBsAg protein powders were dissolved into 1 ml PBS to prepare application solution. For intramuscular injection, 50 μl CpG application solution and 1 μl HBsAg application solution were first mixed thoroughly and then placed on ice for 10 minutes before the injection.
6. Control CpGODN sequence:
5'-TCgTCgTTTTgTCgTTTTgTcgTT-3'[2006]

Figure 7:
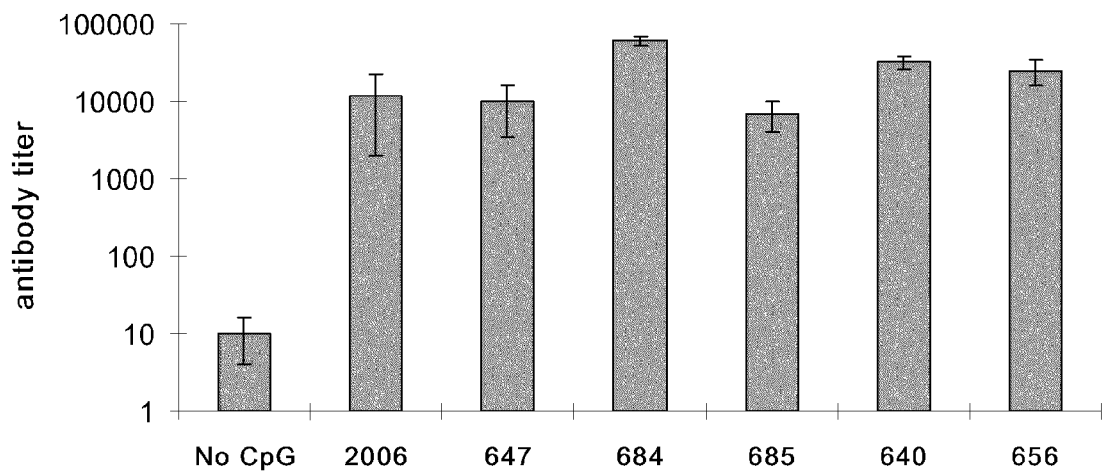
FIG. 7 shows the effects of different CpG ODNs on antibody production stimulated by HBsAg.

II. Methods
1. Mice grouping: 10 mice/group (the dosage of HBV vaccine is 1 μg/mouse, and the content of Al adjuvant is 25 μg/ml)
  1) HBsAg group
  2) HBsAg+2006(100 μg) group
  3) HBsAg+647(100 μg) group
  4) HBsAg+684(100 μg) group
  5) HBsAg+685(100 μg) group
  6) HBsAg+640(100 μg) group
  7) HBsAg+656(100 μg) group
2. The effects of different CPG ODNs on antibody production stimulated by HBsAg The mice were inoculated through tibialis anterior with HBsAg application solution and application solutions of CpG ODNs with different sequences. Blood was drawn from the caudal vein of the mice three days prior to the inoculation (negative serum) and four weeks after the inoculation, immediately followed by adding 2 μl of sodium heparin to each 10 μl of the blood for the purpose of anticoagulation (Shanghai Zhixin Chemical Ltd. 0.2 g heparin was weighted and dissolved in 100 ml $ddH_2O$ to obtain a concentration of 0.2%, and the resultant solution was sterilized under a pressure of 15 pounds for 20 minutes). The blood sample was centrifuged at 4,000 rpm for 20 minutes under 4° C. The plasma in the upper layer was collected and then stored at −20° C. ELISA was used to assay HbsAb titer (As shown in Example 3). The result of the assay indicates when used as adjuvants, all the CpGODNs with different sequences can improve the HbsAb titers produced by mice, though to different extents. Compared with using HBsAg vaccine alone, HBsAg+CpG can significantly elicit mice to produce a relatively high level of HBsAb. The result of the variance analysis showed a significant difference (P<0.05). The comparison of antibody titers among different groups is shown in FIG. 7.

Example 11

The Effects of Different Dosages of CPG ODN on Antibody Production Stimulated by HBsAg I. Animals and Regents
1. Animals: BALB/c mouse, female, aged from 6-8 weeks (available from Beijing Weitonglihua Experimental Animal Ltd.).
2. HBsAg: containing no Al adjuvant, purchased from Beijing Institute of Biological Product.
3. CpGODN: synthesized by Shanghai Shenggong Biotechnology Service Ltd.
4. CpGODN formulation different dosages of CpG ODN were dissolved into 50 μl PBS to prepare CpG ODN solution with corresponding concentrations.
5. HBsAg formulation: 1 mg lyophilized HBsAg protein powders were dissolved into 1 ml PBS to prepare application solution. For intramuscular injection, 50 μl CpG ODN solution and 1 μl HBsAg application solution were first mixed thoroughly and then placed on ice for 10 minutes before the injection (the dosage of HBV vaccine is 1 μg/mouse, and the content of Al adjuvant is 25 μg/ml).

Figure 8:
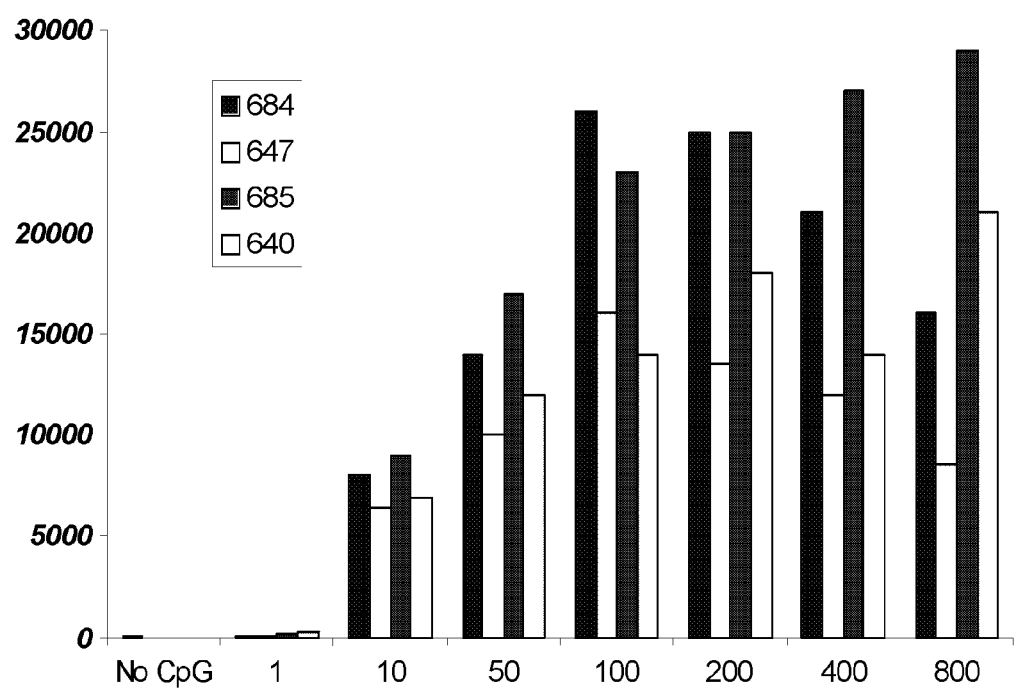
FIG. 8 shows the effects of different dosages of CpG ODN on antibody production stimulated by HBsAg.

II. Methods
1. Mice grouping: 10 mice/group (the dosage of HBV vaccine is 1 μg/mouse, and the content of Al adjuvant is 25 μg/ml)
   HBsAg group
   HBsAg+CpG(684)(1 μg) group
   HBsAg+CpG(647)(1 μg) group
   HBsAg+CpG(685)(1 μg) group
   HBsAg+CpG(640)(1 μg) group
   HBsAg+CpG(684)(10 μg) group
   HBsAg+CpG(647)(10 μg) group
   HBsAg+CpG(685)(10 μg) group
   HBsAg+CpG(640)(10 μg) group
   HBsAg+CpG(684)(50 μg) group
   HBsAg+CpG(647)(50 μg) group
   HBsAg+CpG(685)(50 μg) group
   HBsAg+CpG(640)(50 μg) group
   HBsAg+CpG(684)(100 μg) group
   HBsAg+CpG(647)(100 μg) group
   HBsAg+CpG(685)(100 μg) group
   HBsAg+CpG(640)(100 μg) group
   HBsAg+CpG(684)(200 μg) group
   HBsAg+CpG(647)(200 μg) group
   HBsAg+CpG(685)(200 μg) group
   HBsAg+CpG(640)(200 μg) group
   HBsAg+CpG(684)(400 μg) group
   HBsAg+CpG(647)(400 μg) group
   HBsAg+CpG(685)(400 μg) group
   HBsAg+CpG(640)(400 μg) group
   HBsAg+CpG(684)(800 μg) group
   HBsAg+CpG(647)(800 μg) group
   HBsAg+CpG(685)(800 μg) group
   HBsAg+CpG(640)(800 μg) group
2. The effects of different dosages of CPG ODN on antibody production stimulated by HBsAg: The mice were inoculated through tibialis anterior with HBsAg and different dosages of CpG ODN. Blood was drawn from the caudal vein of the mice three days prior to the inoculation (negative serum) and four weeks after the inoculation, immediately followed by adding 2 μl of sodium heparin to each 10 μl of the blood for the purpose of anticoagulation (0.2 g heparin was weighted and dissolved in 100 ml ddH$_2$O to obtain a concentration of 0.2%, and the resultant solution was sterilized under a pressure of 15 pounds for 20 minutes). The blood sample was centrifuged at 4,000 rpm for 20 minutes under 4□. The plasma in the upper layer was collected and then stored at −20° C. ELISA was used to assay HbsAb titer (As shown in Example 3). The result of the assay indicates, though to different extents, the CpGODN in all the dosages can improve the HbsAb titers produced by mice. When compared with using HBsAg alone, the CpGODN can significantly improved the HBsAb titer produce by mouse, so long as the dosage of CpG ODN used is equal to or more than 10 μg (P<0.05). The comparison of antibody titers among different groups is shown in FIG. 8.

Example 12

The Effects of the Combination Use of Aluminum Adjuvant and Different Dosages of CPG ODN on Antibody Production Stimulated by HBsAg I. Animals and Regents
1. Animals: BALB/c mouse, female, aged from 6-8 weeks (available from Beijing Weitonglihua Experimental Animal Ltd.).
2. HBsAg: containing Al adjuvant (25 mg Al$^{3+}$/mg HBsAg), purchased from Beijing Institute of Biological Product.
3. CpGODN: synthesized by Shanghai Shenggong Biotechnology Service Ltd.
4. CpGODN formulation: different dosages of CpG ODN were dissolved into 50 μl PBS to prepare CpG ODN solution with corresponding concentrations.
5. HBsAg formulation: 1 mg lyophilized HBsAg protein powders were dissolved into 1 ml PBS to prepare application solution. For intramuscular injection, 50 μl CpG ODN solution and 1 μl HBsAg (25 mg Al$^{3+}$/mg HBsAg) were first mixed thoroughly and then placed on ice for 10 minutes before the injection (the dosage of HBV vaccine is 1 μg/mouse, and the content of Al adjuvant is 25 μg/ml).

Figure 9:
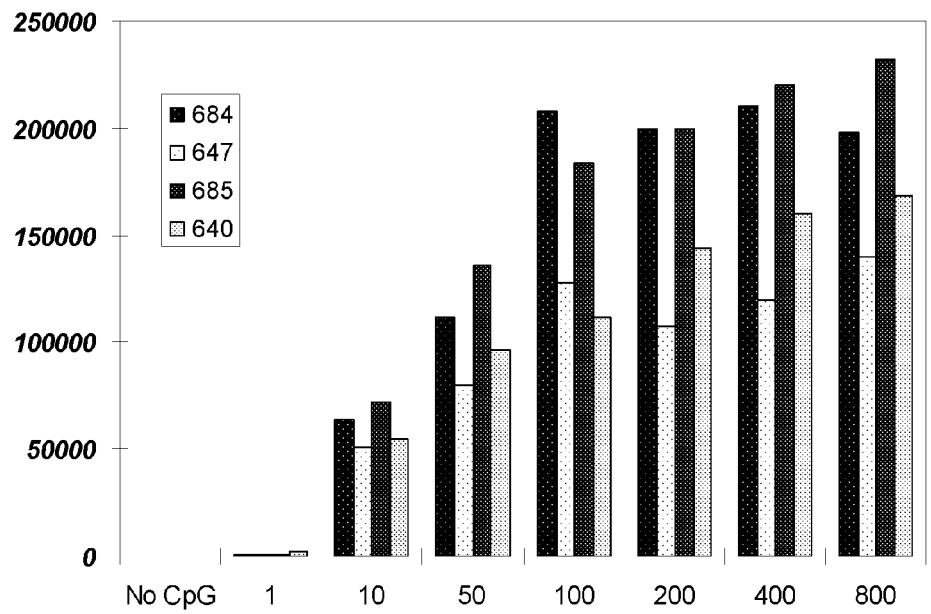
FIG. 9 shows the effects of the combination use of aluminum adjuvant and different dosages of a CpG ODN on antibody production stimulated by HBsAg.

II. Methods
1. Mice grouping: 10 mice/group
   1) HBsAg (25 mg Al$^{3+}$/mg HBsAg) group
   2) HBsAg (25 mg Al$^{3+}$/mg HBsAg)+CpG(684)(1 μg) group
   3) HBsAg (25 mg Al$^{3+}$/mg HBsAg)+CpG(647)(1 μg) group
   4) HBsAg (25 mg Al$^{3+}$/mg HBsAg)+CpG(685)(1 μg) group
   5) HBsAg (25 mg Al$^{3+}$/mg HBsAg)+CpG(640)(1 μg) group
   6) HBsAg (25 mg Al$^{3+}$/mg HBsAg)+CpG(684)(10 μg) group
   7) HBsAg (25 mg Al$^{3+}$/mg HBsAg)+CpG(647)(10 μg) group
   8) HBsAg (25 mg Al$^{3+}$/mg HBsAg)+CpG(685)(10 μg) group
   9) HBsAg (25 mg Al$^{3+}$/mg HBsAg)+CpG(640)(10 μg) group
   10) HBsAg (25 mg Al$^{3+}$/mg HBsAg)+CpG(684)(50 μg) group 11) HBsAg (25 mg Al$^{3+}$/mg HBsAg)+CpG(647)(50 μg) group 12) HBsAg (25 mg Al$^{3+}$/mg HBsAg)+CpG(685)(50 μg) group 13) HBsAg (25 mg Al$^{3+}$/mg HBsAg)+CpG(640)(50 μg) group 14) HBsAg (25 mg Al$^{3+}$/mg HBsAg)+CpG(684)(100 μg) group 15) HBsAg (25 mg Al$^{3+}$/mg HBsAg)+CpG(647)(100 μg) group 16) HBsAg (25 mg Al$^{3+}$/mg HBsAg)+CpG(685)(100 μg) group 17) HBsAg (25 mg Al$^{3+}$/mg HBsAg)+CpG(640)(100 μg) group 18) HBsAg (25 mg Al$^{3+}$/mg HBsAg)+CpG(684)(200 μg) group 19) HBsAg (25 mg Al$^{3+}$/mg HBsAg)+CpG(647)(200 μg) group 20) HBsAg (25 mg Al$^{3+}$/mg HBsAg)+CpG(685)(200 μg) group 21) HBsAg (25 mg Al$^{3+}$/mg HBsAg)+CpG(640)(200 μg) group 22) HBsAg (25 mg Al$^{3+}$/mg HBsAg)+CpG(684)(400 μg) group 23) HBsAg (25 mg Al$^{3+}$/mg HBsAg)+CpG(647)(400 μg) group 24) HBsAg (25 mg Al$^{3+}$/mg HBsAg)+CpG(685)(400 μg) group 25) HBsAg (25 mg Al$^{3+}$/mg HBsAg)+CpG(640)(400 μg) group 26) HBsAg (25 mg Al$^{3+}$/mg HBsAg)+CpG(684)(800 μg) group 27) HBsAg (25 mg Al$^{3+}$/mg HBsAg)+CpG(647)(800 μg) group 28) HBsAg (25 mg Al$^{3+}$/mg HBsAg)+CpG(685)(800 μg) group 29) HBsAg (25 mg Al$^{3+}$/mg HBsAg)+CpG(640)(800 μg) group 2. The combination use of aluminum adjuvant and different dosages of CPG ODN on antibody production stimulated by HBsAg: The mice were inoculated through tibialis anterior with HBsAg and different dosages of CpG ODN. Blood was drawn from the caudal vein of the mice three days prior to the inoculation (negative serum) and four weeks after the inoculation, immediately followed by adding 2 μl of sodium heparin to each 10 μl of the blood for the purpose of anticoagulation (0.2 g heparin was weighted and dissolved in 100 ml ddH$_2$O to obtain a concentration of 0.2%, and the resultant solution was sterilized under a pressure of 15 pounds for 20 minutes). The blood sample was centrifuged at 4,000 rpm for 20 minutes under 4° C. The plasma in the upper layer was collected and then stored at −20° C. ELISA was used to assay HbsAb titer (As shown in Example 3). The result of the assay indicates, though to different extents, the CpGODN in all the dosages can improve the HbsAb titers produced by mice. Compared with the combination of HBsAg and Al adjuvant (25 mg Al$^{3+}$/mg HBsAg), all the combination use of CpGODN and HBsAg (containing no Al adjuvant) can significantly improved the HBsAb titer produce by mouse (P<0.05), so long as the dosage of the CpGODN used is equal to or more than 10 μg. The comparison of antibody titers among different groups is shown in FIG. 9.

Example 13

The Enhancement Effect of the Combination Use of CpG ODN and Al Adjuvant on the Immune Effect of HBsAg I. Animals and Regents 1. Animals: BALB/c mouse, female, aged from 6-8 weeks (available from Beijing Weitonglihua Experimental Animal Ltd.).

2. HBsAg (containing Al adjuvant), HBsAg (containing no Al adjuvant), purchased from Beijing Institute of Biological Product.

3. CpGODN: synthesized by Shanghai Shenggong Biotechnology Service Ltd.

4. CpGODN formulation: 100 μg CpG ODN was dissolved into 50 μl PBS to prepare application solution.

5. HBsAg formulation: 1 mg lyophilized HBsAg protein powders were dissolved into 1 ml PBS to prepare application solution. For intramuscular injection, 50 μl CpG ODN application solution and 1 μl HBsAg (containing or not containing Al adjuvant) were first mixed thoroughly and then placed on ice for 10 minutes before the injection (the dosage of HBV vaccine is 1 μg/mouse, and the content of Al adjuvant is 25 μg/ml).

II. Methods

1. Mice grouping: 10 mice/group

HBsAg group

HBsAg containing Al adjuvant (25 mg Al$^{3+}$/mg HBsAg) group

3) HBsAg+CpG (684) (100 μg) group

4) HBsAg+CpG (647) (100 μg) group

5) HBsAg+CpG (685) (100 μg) group

6) HBsAg+CpG (640) (100 μg) group

Figure 10:
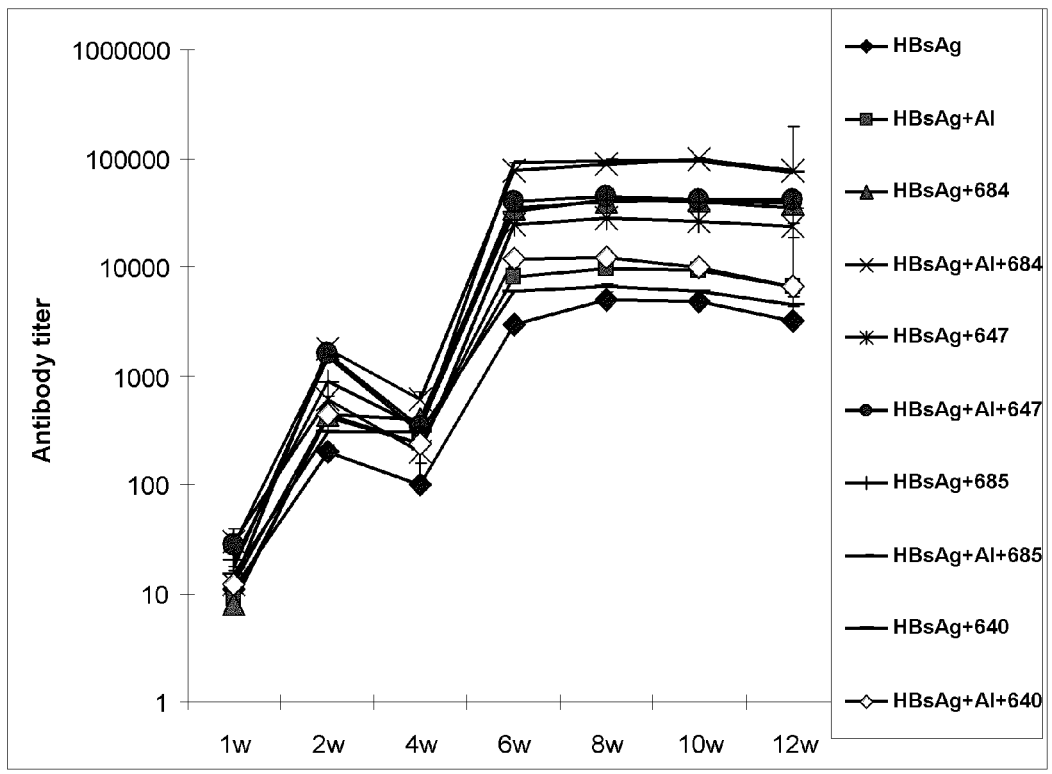
FIG. 10 shows the enhancement effect of the combination use of CpG ODN and an aluminum adjuvant on the immune effect of HBsAg.

7) HBsAg containing Al adjuvant (25 mg Al$^{3+}$/mg HBsAg)+CpG (684) (100 μg) group 8) HBsAg containing Al adjuvant (25 mg Al$^{3+}$/mg HBsAg)+CpG (647) (100 μg) group 9) HBsAg containing Al adjuvant (25 mg Al$^{3+}$/mg HBsAg)+CpG (685) (100 μg) group 10) HBsAg containing Al adjuvant (25 mg Al$^{3+}$/mg HBsAg)+CpG (640) (100 μg) group 2. The enhancement effect of the combination use of CpG ODN and Al adjuvant on the immune effect of HBsAg: The experimental mice were divided into four groups, i.e., HBsAg group, HBsAg containing Al adjuvant (25 mg Al$^{3+}$/mg HBsAg) group, HBsAg+CpGODN group, and HBsAg containing Al adjuvant (25 mg Al$^{3+}$/mg HBsAg)+CpGODN group. The mice were inoculated according to different groups through tibialis anterior. Blood was drawn from the caudal vein of the mice three days prior to the inoculation (negative serum), immediately followed by adding 2 μl of sodium heparin to each 10 μl of the blood for the purpose of anticoagulation (0.2 g heparin was weighted and dissolved in 100 ml ddH$_2$O to obtain a concentration of 0.2%, and the resultant solution was sterilized under a pressure of 15 pounds for 20 minutes). The blood sample was centrifuged at 4,000 rpm for 20 minutes under 4° C. The plasma in the upper layer was collected and then stored at −20° C. The mice were boosted 4 weeks after the initial inoculation (week 0). Blood was drawn from the caudal vein of the mice 1 week, 2 weeks, 4 weeks, 6 weeks, 8 weeks, 10 weeks and 12 weeks after the inoculation. Plasma was separated from the blood and ELISA was used to assay HbsAb titer (As shown in Example 3). The result of the assay indicates, when compared with HBsAg group or HBsAg containing Al adjuvant (25 mg $Al^{3+}$/mg HBsAg) group, the use of CpGODN alone or in combination with Al adjuvant both can improve the HBsAb titers. All the results of the variance analyses showed significant differences ($P<0.05$). The HBsAb titer is the highest when CpGODN is used in combination with Al adjuvant. The comparison of antibody titers among different groups is shown in FIG. 10.

Example 14

The Comparison of the Subtypes of the Antibody Produced by the Stimulation of HbsAg and Different Adjuvants I. Animals and Regents 1. Animals: BALB/c mouse, female, aged from 6-8 weeks (available from Beijing Weitonglihua Experimental Animal Ltd.).

2. HBsAg (containing Al adjuvant), HBsAg (containing no Al adjuvant), purchased from Beijing Institute of Biological Product.

3. CpGODN: synthesized by Shanghai Shenggong Biotechnology Service Ltd.

4. CpGODN formulation: 100 µg CpG ODN was dissolved into 50 µl PBS to prepare application solution.

5. HBsAg formulation: 1 mg lyophilized HBsAg protein powders were dissolved into 1 ml PBS to prepare application solution. For intramuscular injection, 50 µl CpG ODN application solution and 1 µl HBsAg (containing or not containing Al adjuvant) application solution were first mixed thoroughly and then placed on ice for 10 minutes before the injection.

HBsAg (containing no Al adjuvant, available from Beijing Institute of Biological Product) formulation: 1 mg lyophilized HBsAg protein powders were dissolved into 1 ml PBS to prepare application solution.

6. HRP labeled goat-anti-mouse IgG2a and IgG1: product of Serotec Co.

7. Regents formulation:
PBS: 1000 ml

| NaCl | 8 g (Beijing Chemical Plant) |
| KCl | 0.2 g (Beijing Chemical Plant) |
| $Na_2HPO_4 \cdot 12H_2O$ | 2.9 g (Beijing Chemical Plant) |
| $KH_2PO_4$ | 0.2 g (Beijing Chemical Plant) |

After sufficiently dissolved in 800 ml ultra pure water, the resultant solution was adjusted to a pH of 7.2-7.4 with HCl or NaOH, and made up to a volume of 1000 ml.

Coating solution: 100 ml

| PBS | 80 ml |
| 50% glutaraldehyde | 1.6 ml (Beijing Chemical Plant) |

After sufficiently dissolved, the resultant solution was made up by PBS to a volume of 100 ml.

Washing solution: 500 ml

| PBS | 400 ml |
| Tween20 | 0.5 ml (Beijing Chemical Plant) |
| NaCl | 14.625 g (Beijing Chemical Plant) |

After sufficiently dissolved, the resultant solution was made up by PBS to a volume of 500 ml.

Block solution: 100 ml

| PBS | 80 ml |
| Skimmed milk | 5 g (Beijing Dingguo Biotechnology Ltd.) |
| BSA | 1 g (Beijing Dingguo Biotechnology Ltd.) |

After sufficiently dissolved, the resultant solution was made up by PBS to a volume of 100 ml, followed by the addition of 0.05 g sodium azide.

Sample diluent: 1000 ml

| Tris | 2.42 g (Beijing Chemical Plant) |
| NaCl | 8.77 g (Beijing Chemical Plant) |

After sufficiently dissolved in 800 ml ultra pure water, the resultant solution was adjusted to a pH of 7.1 with HCl, followed by the addition of

| BSA | 1 g |
| Tween20 | 0.5 ml | made up to a volume of 1000 ml with ultra pure water.
Substrate Solution:
Solution A:

| Citric acid | 19.2 g (Beijing Chemical Plant) |

After sufficiently dissolved in 800 ml ultra pure water, the resultant solution was made up to a volume of 1000 ml by ultra pure water.

Solution B:

| $Na_2HPO_4 \cdot 12H_2O$ | 71.7 g (Beijing Chemical Plant) |

After sufficiently dissolved in 800 ml ultra pure water, the resultant solution was made up to a volume of 1000 ml by ultra pure water.

Substrate Solution:

| Solution A | 47.276 ml |
| Solution B | 50 ml |

Above volumes of Solution A and Solution B were taken respectively and mixed, followed by filtration through a 0.22 µm filter to remove bacteria.

Stop solution: 100 ml

| | |
|---|---|
| Concentrated H$_2$SO$_4$ | 20 ml (Beijing Chemical Plant) | slowly added into 80 ml ultra pure water while stirring.

Mice Immunization

1. Mice grouping
   1) HBsAg group
   2) HBsAg+CpG(684)(100 μg) group
   3) HBsAg+CpG(647)(100 μg) group
   4) HBsAg+CpG(685)(100 μg) group
   5) HBsAg+CpG(640)(100 μg) group
   6) HBsAg (25 mg Al$^{3+}$/mg HBsAg)+CpG(684)(100 μg) group
   7) HBsAg (25 mg Al$^{3+}$/mg HBsAg)+CpG(647)(100 μg) group
   8) HBsAg (25 mg Al$^{3+}$/mg HBsAg)+CpG(685)(100 μg) group
   9) HBsAg (25 mg Al$^{3+}$/mg HBsAg)+CpG(640)(100 μg) group 2. Mice immunization: On week 0 and week 4, mice were inoculated according to different groups through tibialis anterior. Blood was drawn from the caudal vein of the mice three days prior to the inoculation (negative serum), immediately followed by adding 2 μl of sodium heparin to each 10 μl of the blood for the purpose of anticoagulation (0.2 g heparin was weighted and dissolved in 100 ml ddH$_2$O to obtain a concentration of 0.2%, and the resultant solution was sterilized under a pressure of 15 pounds for 20 minutes). The blood sample was centrifuged at 4,000 rpm for 20 minutes under 4° C. The plasma in the upper layer was collected and then stored at −20° C. (the dosage of HBV vaccine is 1 μg/mouse, and the content of Al adjuvant is 25 μg/ml)

II. Methods

1. Coating: 100 μl HBsAg (1 mg/ml) was added into 10 ml coating solution. The diluted HBsAg was added into each well of an ELISA plate, which was then left stand overnight under a temperature of 4° C.

2. Washing: The next day, the liquid left in the wells of the plate was removed completely, and 300 μl washing solution was added into each well. Before removing the washing solution, the plate was left stand for 3 minute at room temperature. Finally, the plate was dried by tapping on an absorbent paper. Same washing procedure was repeated for 3 times.

3. Blocking: 300 μl blocking solution was added into the wells of the ELISA plate, and was left stand for 2 hs at room temperature.

4. Adding samples to be tested: Same washing procedures described in step 2 were applied. Samples to be tested were diluted into different concentrations with sample diluent before being added. 100 μl diluted sample was added into wells in duplicate and was left stand for 2 hs at room temperature.

5. Adding HRP labeled goat-anti-mouse IgG2a and IgG1: Same washing procedures described in step 2 were applied. IRP labeled goat-anti-mouse IgG2a and IgG1 was diluted with sample diluent (1:1000). 100 μl diluted IRP labeled goat-anti-mouse IgG2a and IgG1 was added into wells and was left stand for 2 hs in darkness at room temperature.

6. Adding substrate solution: Same washing procedures described in step 2 were applied. 100 μl freshly made substrate solution was added into each well, and left stand for 20 minutes in darkness at room temperature.

7. Adding stop solution: The ELISA plate was incubated for 20 minutes, after which 50 μl stop solution was added into each well.

8. ELISA assay (A492 nm): ELISA assay (A492 nm) was carried out within 5 minutes after the addition of the stop solution.

9. Determination of a positive value: A positive value is defined where the OD value of a sample/the OD value of the negative control is 2 or more.

Figure 11:
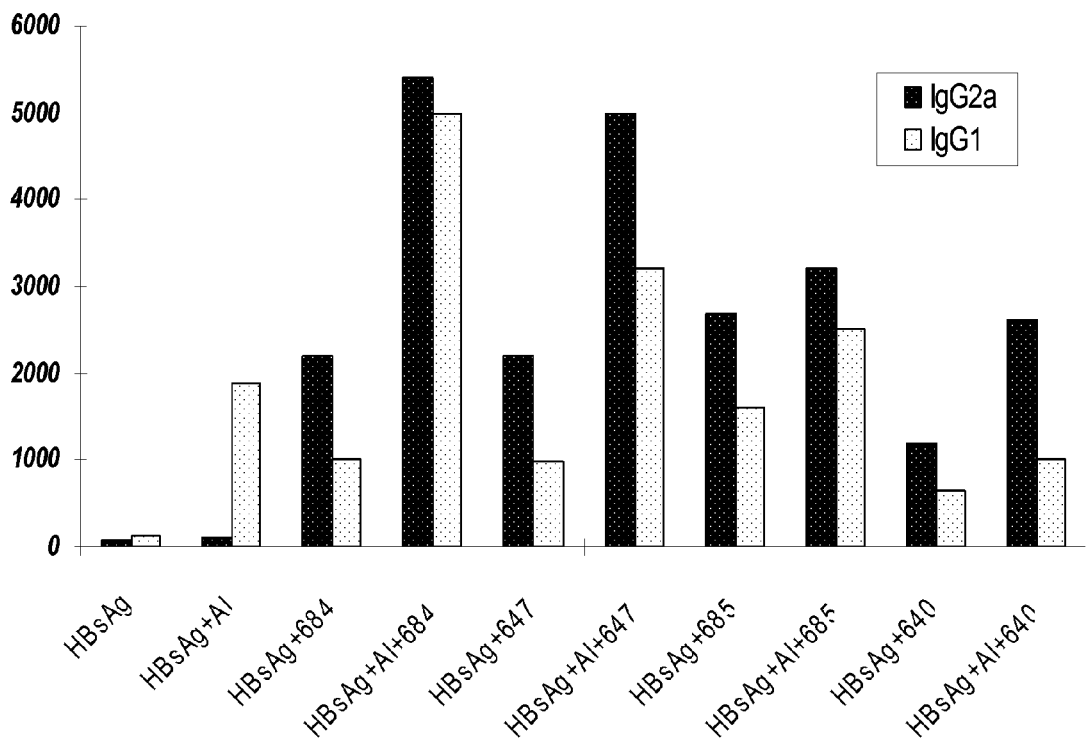
FIG. 11 shows the comparison of the subtypes of the antibody produced by the stimulation of HbsAg in combination with different adjuvants.

Compared with Al adjuvant, the use of CpG as adjuvant produced a higher level of IgG2a antibody. The result of variance analysis (See FIG. 11) showed significant differences (P<0.05).

Assay of CTL Specific Killing (1) Preparation of effector cell: 12 weeks after vaccination, the spleen of the mice was removed under sterile condition and placed into a dish containing IMDM (Gibcol Co.) supplemented with 10% calf serum. The spleen was gently ground with a frosted glass plate, and then filtered through a filter screen having 200 meshes. 3-5 ml RBC lysis solution (139.6 mmol/L NH$_4$Cl, 16.96 mmol/L Tris, pH was adjusted to 7.2 with 1 mol/HCl) was added to the filtered fluid, and the resultant was left stand for 10 minutes. The spleen cells were washed twice with normal saline before being counted. The spleen cells was adjusted to a concentration of 3×10$^7$/ml with IMDM containing 10% calf serum. Mitomycin (Sigma, formulated with IMDM containing no serum to a concentration of 500 μg/ml) was added into P815 cells (ATCC) transfected with HbsAg gene to a final concentration of 50 μg/ml. The resultant was incubated at 37° C. for 2 hs and then washed 3 times with normal saline. 1×10$^6$ P815 cells were co-cultured with the spleen cells for 5 days at 37° C. in 5% CO$_2$, after which the speen cells were collected as effector cells.

(2) $^{51}$Cr labeled target cells: 100 μl $^{51}$Cr (Perkin Elmer life Science) was added into 1×10$^6$ P815 cells transfected with HbsAg gene. The resultant was incubated at 37° C. for 1 h, during which the P815 cells were gently stirred every 5-10 minutes. The P815 cells were used as target cells after being washed three times with IMDM containing 10% calf serum.

(3) CTL killing test: The effector cells were diluted into different concentrations with IMDM containing 10% calf serum, into which $^{51}$Cr labeled P815 cells were added to a final ratio of effector cells: target cells of 100:1~112.5:1. After incubated at 37° C. for 4 hs, the supernatant of the cells was collected and tested for c.p.m value.

Figure 12:
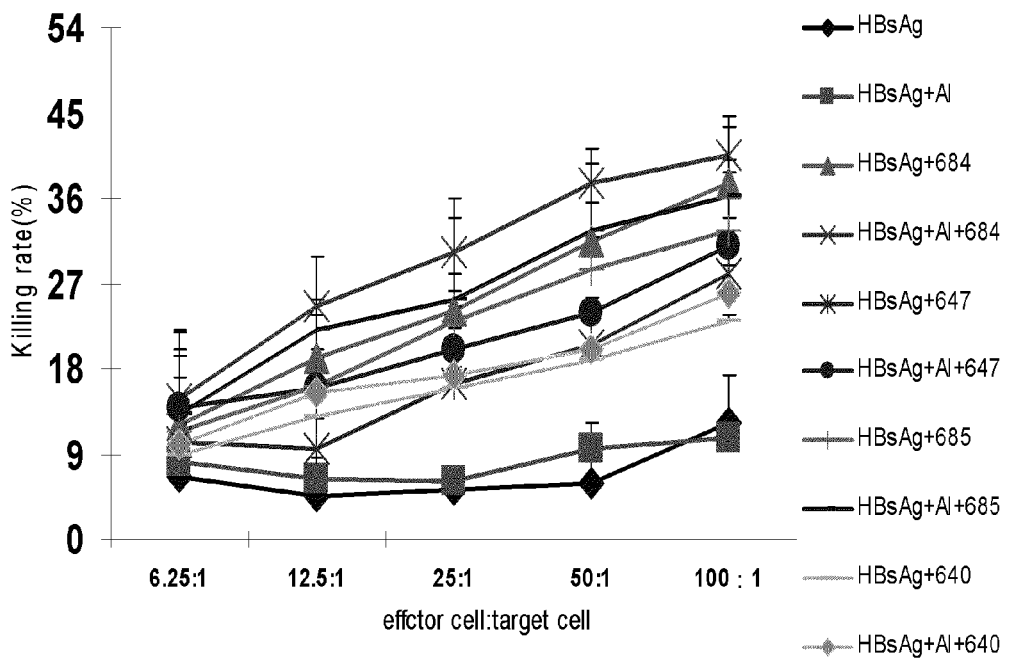
FIG. 12 shows the effect of CpG ODN on HBV specific CTL induced by HBsAg.

(4) The result indicated as an adjuvant, CpGODN can significantly improve HBV-specific CTL activity produced by mice stimulated with HbsAg. Compared with Al adjuvant+HbsAg, CpGODN+HbsAg elicited a stronger HBV-specific CTL activity (P<0.05) (See FIG. 12).

Example 15

CpG ODN Enhanced the Response of Suckling Mice to HBV Vaccine

I. Animals and Regents

1. Animals: BALB/c suckling mouse, female, aged from 6-8 days (available from Beijing Weitonglihua Experimental Animal Ltd.).

2. HBsAg: containing Al adjuvant (25 mg Al$^{3+}$/mg HBsAg) or containing no Al adjuvant, purchased from Beijing Institute of Biological Product.

3. CpGODN: synthesized by Shanghai Shenggong Biotechnology Service Ltd.

4. CpGODN formulation: 100 μg CpG ODN were dissolved into 10 μl PBS to prepare application solutions.

5. HBsAg formulation: 1 mg lyophilized HBsAg protein powders were dissolved into 1 ml PBS to prepare application solution. For intramuscular injection, 10 μl CpG ODN application solution and 1 μl HBsAg (containing Al adjuvant or not containing Al adjuvant) application solution were first mixed thoroughly and then placed on ice for 10 minutes before the injection.

II. Methods

Figure 13:
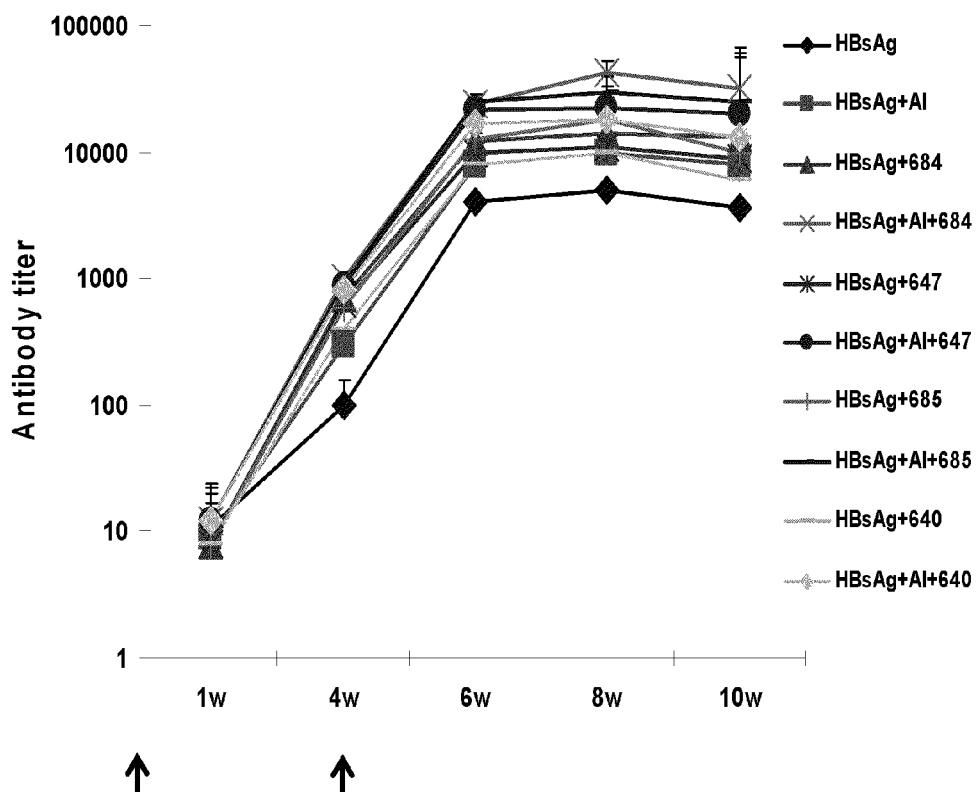
FIG. 13 shows that CpG ODN enhanced the response of suckling mice to HBsAg.

1. Suckling mice grouping: 10 suckling mice/group
    1) HBsAg group
    2) HBsAg+Al adjuvant group
    3) HBsAg+CpG (684) (100 μg) group
    4) HBsAg+CpG (647) (100 μg) group
    5) HBsAg+CpG (685) (100 μg) group
    6) HBsAg+CpG (640) (100 μg) group
    7) HBsAg+CpG(684) (100 μg)+Al adjuvant group
    8) HBsAg+CpG(647) (100 μg)+Al adjuvant group
    9) HBsAg+CpG(685) (100 μg)+Al adjuvant group
    10) HBsAg+CpG(640) (100 μg)+Al adjuvant group 2. Test of whether CpG ODN can enhance the response of suckling mice to HBV vaccines: The experimental suckling mice were divided into four groups, i.e., HBsAg group, HBsAg+Al adjuvant group, HBsAg+CpGODN group, and HBsAg+Al adjuvant+CpGODN group. The suckling mice were inoculated according to different groups through tibialis anterior. The mice were boosted 4 weeks after the initial inoculation (week 0). Blood was drawn 1 week, 4 weeks, 6 weeks, 8 weeks and 10 weeks after the inoculation, immediately followed by adding 2 μl of sodium heparin to each 10 μl of the blood for the purpose of anticoagulation (0.2 g heparin was weighted and dissolved in 100 ml ddH$_2$O to obtain a concentration of 0.2%, and the resultant solution was sterilized under a pressure of 15 pounds for 20 minutes). The blood sample was centrifuged at 4,000 rpm for 20 minutes under 4° C. The plasma in the upper layer was collected and then stored at −20° C. Plasma was separated from the blood and ELISA was used to assay HbsAb titer (As shown in Example 3). The result of the assay indicates, when compared with HBsAg group or HBsAg (25 mg Al$^{3+}$/mg HBsAg) group, the use of CpGODN alone or in combination with Al adjuvant both can improve the HBsAb titers in suckling mice. All the results of the variance analyses showed significant differences ($P<0.05$). The HBsAb titer produced by the suckling mice is the highest when CpGODN is used in combination with Al adjuvant. The comparison of antibody titers among different groups is shown in FIG. 13. The test result of this example indicated CpG ODN can elicit relatively stronger humoral immunity response from individuals having weak humoral immunity response.

Example 16

CpG ODN Enhanced the Response of Aged Mice to HBV Vaccine

I. Animals and Regents

1. Animals: BALB/c mouse, female, aged from 20-24 months (Beijing Weitonglihua Experimental Animal Ltd.).

2. HBsAg: containing Al adjuvant (25 mg Al$^{3+}$/mg HBsAg) or containing no Al adjuvant, purchased from Beijing Institute of Biological Product.

3. CpGODN: synthesized by Shanghai Shenggong Biotechnology Service Ltd.

4. CpGODN formulation: 100 μg CpG ODN were dissolved into 50 μl PBS to prepare application solutions.

5. HBsAg formulation: 1 mg lyophilized HBsAg protein powders were dissolved into 1 ml PBS to prepare application solution. For intramuscular injection, 50 μl CpG ODN application solution and 1 μl HBsAg (containing Al adjuvant or not containing Al adjuvant) were first mixed thoroughly and then placed on ice for 10 minutes before the injection (the dosage of HBV vaccine is 1 μg/mouse, and the content of Al adjuvant is 25 μg/ml).

II. Methods

Figure 14:
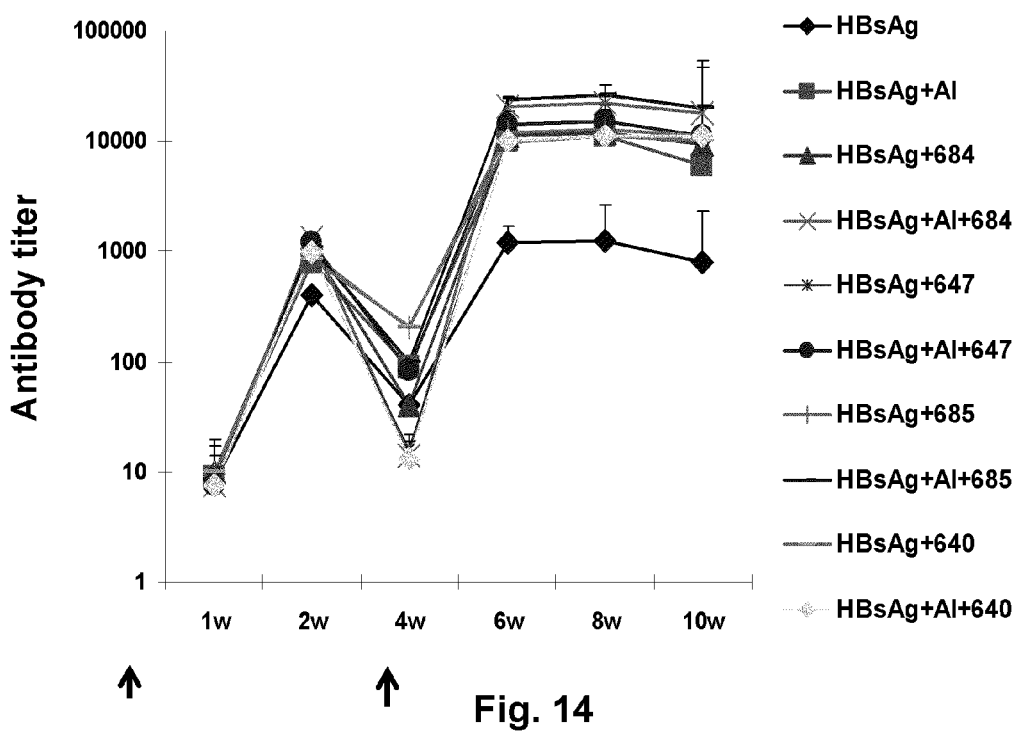
FIG. 14 shows that CpG ODN enhanced the response of aged mice to HBsAg.

1. Mice grouping: 10 mice/group
    1) HBsAg group
    2) HBsAg+Al adjuvant group
    3) HBsAg+CpG(684) (100 μg) group
    4) HBsAg+CpG(647) (100 μg) group
    5) HBsAg+CpG (685) (100 μg) group
    6) HBsAg+CpG (640) (100 μg) group
    7) HBsAg+CpG(684) (100 μg)+Al adjuvant group
    8) HBsAg+CpG(647) (100 μg)+Al adjuvant group
    9) HBsAg+CpG(685) (100 μg)+Al adjuvant group
    10) HBsAg+CpG(640) (100 μg)+Al adjuvant group 2. Antibody assay: The aged mice were divided into four groups, i.e., HBsAg group, HBsAg+Al adjuvant group, HBsAg+CpGODN group, and HBsAg+Al adjuvant+CpGODN group. The aged mice were inoculated according to different groups through tibialis anterior. The mice were boosted 4 weeks after the initial inoculation (week 0). Blood was drawn 3 days prior to the inoculation (negative serum), immediately followed by adding 2 μl of sodium heparin to each 10 μl of the blood for the purpose of anticoagulation (0.2 g heparin was weighted and dissolved in 100 ml ddH$_2$O to obtain a concentration of 0.2%, and the resultant solution was sterilized under a pressure of 15 pounds for 20 minutes). The blood sample was centrifuged at 4,000 rpm for 20 minutes under 4° C. The plasma in the upper layer was collected and then stored at −20° C. Blood was drawn 2 weeks, 4 weeks, 6 weeks, 8 weeks, 10 weeks and 12 weeks after the inoculation. Plasma was separated from the blood and ELISA was used to assay HbsAb titer (As shown in Example 3). The result of the assay indicates, when compared with HBsAg group or HBsAg (25 mg Al$^{3+}$/mg HBsAg) group, the use of CpGODN alone or in combination with Al adjuvant both can improve the HBsAb titers in aged mice. All the results of the variance analyses showed significant differences ($P<0.05$). The HBsAb titer produced by the aged mice is the highest when CpGODN is used in combination with Al adjuvant. The comparison of antibody titers among different groups is shown in FIG. 14. The test result of this example indicated CpG ODN can elicit relatively stronger humoral immunity response from individuals having weak humoral immunity response.

Example 17

CpG ODN Enhanced the Response of Rhesus to HBV Vaccine

I. Animals and Regents

1. Animals: rhesus, 2-4 kg, female (Beijing Weitonglihua Experimental Animal Ltd.).

2. HBsAg: containing Al adjuvant (25 mg Al$^{3+}$/mg HBsAg) or containing no Al adjuvant, purchased from Beijing Institute of Biological Product.

3. CpGODN: synthesized by Shanghai Shenggong Biotechnology Service Ltd.

4. CpGODN formulation: 100 μg CpG ODN were dissolved into 50 μl PBS to prepare application solutions.

5. HBsAg formulation: 1 mg lyophilized HBsAg protein powders were dissolved into 1 ml PBS to prepare application solution. For intramuscular injection, 50 μl CpG ODN application solution and 1 μl HBsAg (containing Al adjuvant or not containing Al adjuvant) application solution were first mixed thoroughly and then placed on ice for 10 minutes before the injection (the dosage of HBV vaccine is 1 μg/rhesus, and the content of Al adjuvant is 25 μg/ml).

Figure 15:
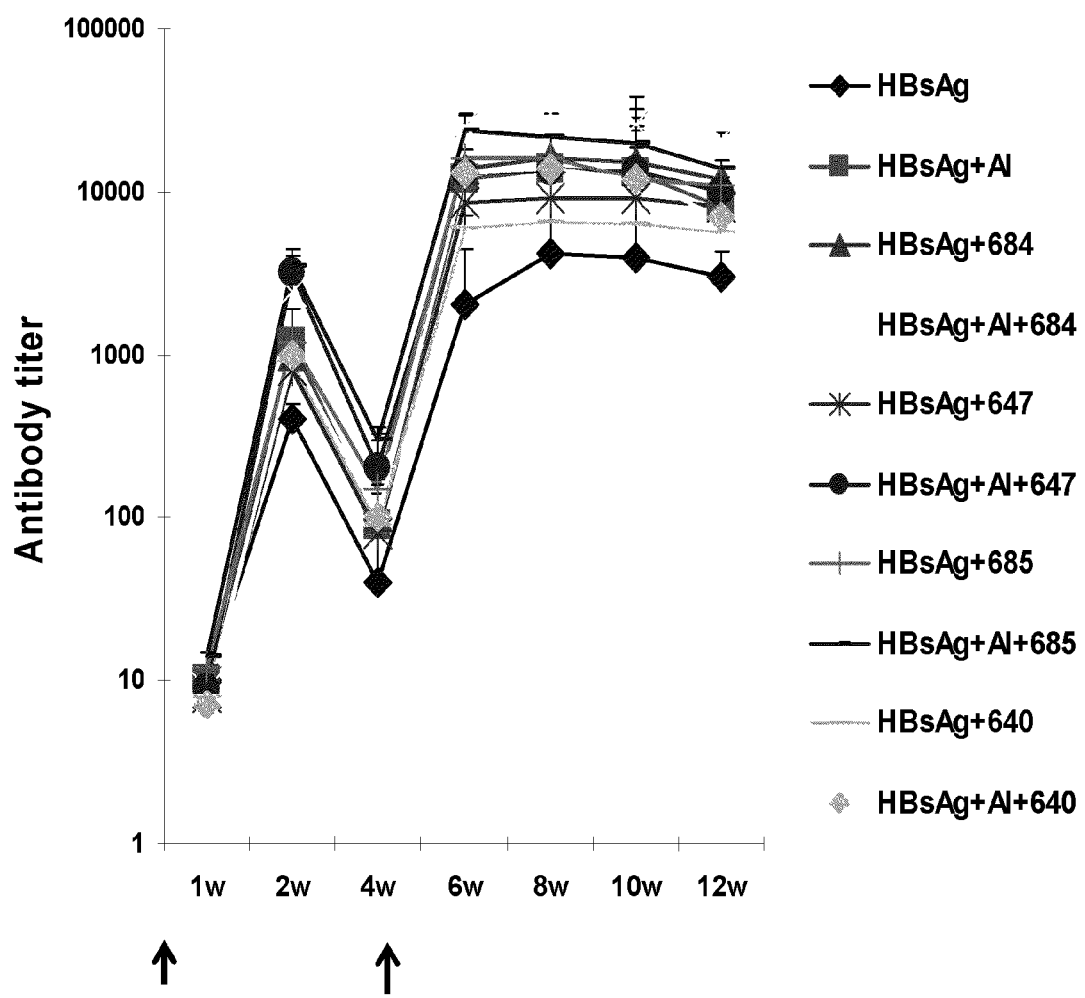
FIG. 15 shows that CpG ODN enhanced the response of rhesus to HBsAg.

II. Method
1. Rhesuses grouping:
1) HBsAg(10 μg)+Al adjuvant group
2) HBsAg(10 μg)+CpG (684) (1000 μg) group
3) HBsAg(10 μg)+CpG (647) (1000 μg) group
4) HBsAg(10 μg)+CpG (685) (1000 μg) group
5) HBsAg(10 μg)+CpG (640) (1000 μg) group
6) HBsAg(10 μg)+CpG (684) (1000 μg)+Al adjuvant group
7) HBsAg(10 μg)+CpG (647) (1000 μg)+Al adjuvant group
8) HBsAg(10 μg)+CpG (685) (1000 μg)+Al adjuvant group
9) HBsAg(10 μg)+CpG (640) (1000 μg)+Al adjuvant group 2. Antibody assay: Blood was drawn from the rhesuses before inoculation, and negative plasma was isolated from the blood. The rhesuses were inoculated according to different groups through deltoid. The rhesuses were boosted 4 weeks after the initial inoculation (week 0). Blood was drawn 2 weeks, 4 weeks, 6 weeks, 8 weeks, 10 weeks and 12 weeks after the inoculation. Plasma was separated form the blood and ELISA was used to assay HbsAb titer. The result of the assay indicates, when compared with HBsAg group or HBsAg (25 mg $Al^{3+}$/mg HBsAg) group, the use of CpGODN alone or in combination with Al adjuvant both can improve the HBsAb titers in rhesuses. All the results of the variance analyses showed significant differences ($P<0.05$). The HBsAb titer produced by the rhesuses is the highest when CpGODN is used in combination with Al adjuvant. The comparison of antibody titers among different groups is shown in FIG. 15.

---

What is claimed is:

1. A method of improving immunogenicity of a vaccine, comprising coadministering said vaccine to a subject with a single strand deoxynucleotide, comprising the nucleotide sequence of SEQ ID NO: 167 and said vaccine.

2. The method of claim 1, wherein bases of the deoxynucleotide are modified by one or more modifications selected from the group consisting of non-sulfur modification, sulfur modification, partial sulfur modification, rare base modification, methylation modification, and other modifications where sulfhydryl, Aminolinker C6 and Thiol-C6 S-S are used to couple to other substances.

3. The method of claim 1, wherein the single strand deoxynucleotide is used alone or in combination with a non-nucleic acid adjuvant including aluminum adjuvant, Freund's adjuvant, MPL, or emulsion.

4. The method of claim 1, wherein the single strand deoxynucleotide is admixed with or chemically coupled to a vaccine, or the single strand deoxynucleotide is cloned into a DNA vaccine.

5. The method of claim 1, wherein the vaccine is selected from the group consisting of hepatitis B virus blood-derived vaccine, hepatitis B virus genetic engineering protein vaccines, HBV virus vector vaccine, hepatitis B virus bacterium vector vaccine, hepatitis B virus transgenic plant vaccine, rabies virus blood-derived vaccine, rabies virus genetic engineering protein vaccines, rabies virus vector vaccine, rabies virus bacterium vector vaccine, and rabies virus transgenic plant vaccine, and the DNA vaccine is selected from the group consisting of hepatitis B virus DNA vaccine and rabies DNA vaccine.

6. The method of claim 1, further comprising administering non-nucleic acid adjuvants.

7. The method of claim 1, wherein the subject is human.

8. The method of claim 1, wherein the subject is a mammal.

* * * * *

SEQUENCE LISTING

<160> NUMBER OF SEQ ID NOS: 185

<210> SEQ ID NO 1
<211> LENGTH: 22
<212> TYPE: DNA
<213> ORGANISM: Artificial Sequence
<220> FEATURE:
<223> OTHER INFORMATION: synthetic deoxynucleotide

<400> SEQUENCE: 1
ggggtcgttc gtcgttgggg gg                                    22

<210> SEQ ID NO 2
<211> LENGTH: 20
<212> TYPE: DNA
<213> ORGANISM: Artificial Sequence
<220> FEATURE:
<223> OTHER INFORMATION: synthetic deoxynucleotide

<400> SEQUENCE: 2
ggggataacg ttgcgggggg                                       20

<210> SEQ ID NO 3
<211> LENGTH: 21
<212> TYPE: DNA
<213> ORGANISM: Artificial Sequence
<220> FEATURE:
<223> OTHER INFORMATION: synthetic deoxynucleotide

<400> SEQUENCE: 3
ggggtgcaac gttcaggggg g                                     21

<210> SEQ ID NO 4
<211> LENGTH: 22
<212> TYPE: DNA
<213> ORGANISM: Artificial Sequence
<220> FEATURE:
<223> OTHER INFORMATION: synthetic deoxynucleotide

<400> SEQUENCE: 4
ggggtcctac gtaggagggg gg                                    22

```
<210> SEQ ID NO 5
<211> LENGTH: 27
<212> TYPE: DNA
<213> ORGANISM: Artificial Sequence
<220> FEATURE:
<223> OTHER INFORMATION: synthetic deoxynucleotide

<400> SEQUENCE: 5
ggggtccatg acgttcctga agggggg                                           27

<210> SEQ ID NO 6
<211> LENGTH: 20
<212> TYPE: DNA
<213> ORGANISM: Artificial Sequence
<220> FEATURE:
<223> OTHER INFORMATION: synthetic deoxynucleotide

<400> SEQUENCE: 6
gggggacgtc gccggggggg                                                   20

<210> SEQ ID NO 7
<211> LENGTH: 20
<212> TYPE: DNA
<213> ORGANISM: Artificial Sequence
<220> FEATURE:
<223> OTHER INFORMATION: synthetic deoxynucleotide

<400> SEQUENCE: 7
ggatccgtac gcatgggggg                                                   20

<210> SEQ ID NO 8
<211> LENGTH: 20
<212> TYPE: DNA
<213> ORGANISM: Artificial Sequence
<220> FEATURE:
<223> OTHER INFORMATION: synthetic deoxynucleotide

<400> SEQUENCE: 8
gggggaatcg attcgggggg                                                   20

<210> SEQ ID NO 9
<211> LENGTH: 24
<212> TYPE: DNA
<213> ORGANISM: Artificial Sequence
<220> FEATURE:
<223> OTHER INFORMATION: synthetic deoxynucleotide

<400> SEQUENCE: 9
gggatgcatc gatgcatcgg gggg                                              24

<210> SEQ ID NO 10
<211> LENGTH: 20
<212> TYPE: DNA
<213> ORGANISM: Artificial Sequence
<220> FEATURE:
<223> OTHER INFORMATION: synthetic deoxynucleotide

<400> SEQUENCE: 10
ggtgcgacgt cgcagggggg                                                   20

<210> SEQ ID NO 11
<211> LENGTH: 18
<212> TYPE: DNA
<213> ORGANISM: Artificial Sequence
<220> FEATURE:
```

<223> OTHER INFORMATION: synthetic deoxynucleotide

<400> SEQUENCE: 11
gggacgtacg tcggggggg                                                18

<210> SEQ ID NO 12
<211> LENGTH: 24
<212> TYPE: DNA
<213> ORGANISM: Artificial Sequence
<220> FEATURE:
<223> OTHER INFORMATION: synthetic deoxynucleotide

<400> SEQUENCE: 12
gggggatcga cgtcgatcgg gggg                                          24

<210> SEQ ID NO 13
<211> LENGTH: 22
<212> TYPE: DNA
<213> ORGANISM: Artificial Sequence
<220> FEATURE:
<223> OTHER INFORMATION: synthetic deoxynucleotide

<400> SEQUENCE: 13
ggcgatcgat cgatcggggg gg                                            22

<210> SEQ ID NO 14
<211> LENGTH: 22
<212> TYPE: DNA
<213> ORGANISM: Artificial Sequence
<220> FEATURE:
<223> OTHER INFORMATION: synthetic deoxynucleotide

<400> SEQUENCE: 14
ggggtcgatc gatcgagggg gg                                            22

<210> SEQ ID NO 15
<211> LENGTH: 20
<212> TYPE: DNA
<213> ORGANISM: Artificial Sequence
<220> FEATURE:
<223> OTHER INFORMATION: synthetic deoxynucleotide

<400> SEQUENCE: 15
ggtcgcgatc gcgaggggggg                                              20

<210> SEQ ID NO 16
<211> LENGTH: 20
<212> TYPE: DNA
<213> ORGANISM: Artificial Sequence
<220> FEATURE:
<223> OTHER INFORMATION: synthetic deoxynucleotide

<400> SEQUENCE: 16
ggggtcaacg ttgagggggg                                               20

<210> SEQ ID NO 17
<211> LENGTH: 28
<212> TYPE: DNA
<213> ORGANISM: Artificial Sequence
<220> FEATURE:
<223> OTHER INFORMATION: synthetic deoxynucleotide

<400> SEQUENCE: 17
gtcgttttcg tcgacgaatt gggggggg                                      28

```
<210> SEQ ID NO 18
<211> LENGTH: 26
<212> TYPE: DNA
<213> ORGANISM: Artificial Sequence
<220> FEATURE:
<223> OTHER INFORMATION: synthetic deoxynucleotide

<400> SEQUENCE: 18
gtcgttatcg tttttcgta gggggg                                           26

<210> SEQ ID NO 19
<211> LENGTH: 18
<212> TYPE: DNA
<213> ORGANISM: Artificial Sequence
<220> FEATURE:
<223> OTHER INFORMATION: synthetic deoxynucleotide

<400> SEQUENCE: 19
ggcgttaacg acgggggg                                                   18

<210> SEQ ID NO 20
<211> LENGTH: 19
<212> TYPE: DNA
<213> ORGANISM: Artificial Sequence
<220> FEATURE:
<223> OTHER INFORMATION: synthetic deoxynucleotide

<400> SEQUENCE: 20
gtcggcacgc gacggggggg                                                 19

<210> SEQ ID NO 21
<211> LENGTH: 20
<212> TYPE: DNA
<213> ORGANISM: Artificial Sequence
<220> FEATURE:
<223> OTHER INFORMATION: synthetic deoxynucleotide

<400> SEQUENCE: 21
ggtgcgacgt cgcagggggg                                                 20

<210> SEQ ID NO 22
<211> LENGTH: 23
<212> TYPE: DNA
<213> ORGANISM: Artificial Sequence
<220> FEATURE:
<223> OTHER INFORMATION: synthetic deoxynucleotide

<400> SEQUENCE: 22
gtctattttg tacgtacgtg ggg                                             23

<210> SEQ ID NO 23
<211> LENGTH: 24
<212> TYPE: DNA
<213> ORGANISM: Artificial Sequence
<220> FEATURE:
<223> OTHER INFORMATION: synthetic deoxynucleotide

<400> SEQUENCE: 23
gacgtcgacg tcgacgtcag gggg                                            24

<210> SEQ ID NO 24
<211> LENGTH: 25
<212> TYPE: DNA
<213> ORGANISM: Artificial Sequence
<220> FEATURE:
<223> OTHER INFORMATION: synthetic deoxynucleotide
```

<400> SEQUENCE: 24
ggggtcgatc gttgctagcg ggggg                                              25

<210> SEQ ID NO 25
<211> LENGTH: 25
<212> TYPE: DNA
<213> ORGANISM: Artificial Sequence
<220> FEATURE:
<223> OTHER INFORMATION: synthetic deoxynucleotide

<400> SEQUENCE: 25
gggggacgtt atcgtattgg ggggg                                              25

<210> SEQ ID NO 26
<211> LENGTH: 32
<212> TYPE: DNA
<213> ORGANISM: Artificial Sequence
<220> FEATURE:
<223> OTHER INFORMATION: synthetic deoxynucleotide

<400> SEQUENCE: 26
ggggtcgtcg tttgtcgtgt gtcgttgggg gg                                      32

<210> SEQ ID NO 27
<211> LENGTH: 20
<212> TYPE: DNA
<213> ORGANISM: Artificial Sequence
<220> FEATURE:
<223> OTHER INFORMATION: synthetic deoxynucleotide

<400> SEQUENCE: 27
acgatcgatc gatcgggggg                                                    20

<210> SEQ ID NO 28
<211> LENGTH: 19
<212> TYPE: DNA
<213> ORGANISM: Artificial Sequence
<220> FEATURE:
<223> OTHER INFORMATION: synthetic deoxynucleotide

<400> SEQUENCE: 28
agacgtctaa cgtcggggg                                                     19

<210> SEQ ID NO 29
<211> LENGTH: 24
<212> TYPE: DNA
<213> ORGANISM: Artificial Sequence
<220> FEATURE:
<223> OTHER INFORMATION: synthetic deoxynucleotide

<400> SEQUENCE: 29
ggggtgctgg ccgtcgttgg gggg                                               24

<210> SEQ ID NO 30
<211> LENGTH: 21
<212> TYPE: DNA
<213> ORGANISM: Artificial Sequence
<220> FEATURE:
<223> OTHER INFORMATION: synthetic deoxynucleotide

<400> SEQUENCE: 30
ggggtcgttg ccgtcggggg g                                                  21

<210> SEQ ID NO 31
<211> LENGTH: 24

```
<212> TYPE: DNA
<213> ORGANISM: Artificial Sequence
<220> FEATURE:
<223> OTHER INFORMATION: synthetic deoxynucleotide

<400> SEQUENCE: 31
accggtatcg atgccggtgg gggg                                          24

<210> SEQ ID NO 32
<211> LENGTH: 28
<212> TYPE: DNA
<213> ORGANISM: Artificial Sequence
<220> FEATURE:
<223> OTHER INFORMATION: synthetic deoxynucleotide

<400> SEQUENCE: 32
ttcgttgcat cgatgcatcg ttgggggg                                      28

<210> SEQ ID NO 33
<211> LENGTH: 21
<212> TYPE: DNA
<213> ORGANISM: Artificial Sequence
<220> FEATURE:
<223> OTHER INFORMATION: synthetic deoxynucleotide

<400> SEQUENCE: 33
ggggacgata cgtcgggggg g                                             21

<210> SEQ ID NO 34
<211> LENGTH: 21
<212> TYPE: DNA
<213> ORGANISM: Artificial Sequence
<220> FEATURE:
<223> OTHER INFORMATION: synthetic deoxynucleotide

<400> SEQUENCE: 34
ggggacgata tcgatggggg g                                             21

<210> SEQ ID NO 35
<211> LENGTH: 20
<212> TYPE: DNA
<213> ORGANISM: Artificial Sequence
<220> FEATURE:
<223> OTHER INFORMATION: synthetic deoxynucleotide

<400> SEQUENCE: 35
ggacgatcga tcgtggggggg                                              20

<210> SEQ ID NO 36
<211> LENGTH: 21
<212> TYPE: DNA
<213> ORGANISM: Artificial Sequence
<220> FEATURE:
<223> OTHER INFORMATION: synthetic deoxynucleotide

<400> SEQUENCE: 36
tcggggacga tcgtcggggg g                                             21

<210> SEQ ID NO 37
<211> LENGTH: 24
<212> TYPE: DNA
<213> ORGANISM: Artificial Sequence
<220> FEATURE:
<223> OTHER INFORMATION: synthetic deoxynucleotide

<400> SEQUENCE: 37
```

| | |
|---|---|
| gggggatcga tatcgatcgg gggg | 24 |

<210> SEQ ID NO 38
<211> LENGTH: 22
<212> TYPE: DNA
<213> ORGANISM: Artificial Sequence
<220> FEATURE:
<223> OTHER INFORMATION: synthetic deoxynucleotide

<400> SEQUENCE: 38

| | |
|---|---|
| ggatcgatcg atcgatgggg gg | 22 |

<210> SEQ ID NO 39
<211> LENGTH: 24
<212> TYPE: DNA
<213> ORGANISM: Artificial Sequence
<220> FEATURE:
<223> OTHER INFORMATION: synthetic deoxynucleotide

<400> SEQUENCE: 39

| | |
|---|---|
| ggtgcatcga tcgatgcagg gggg | 24 |

<210> SEQ ID NO 40
<211> LENGTH: 24
<212> TYPE: DNA
<213> ORGANISM: Artificial Sequence
<220> FEATURE:
<223> OTHER INFORMATION: synthetic deoxynucleotide

<400> SEQUENCE: 40

| | |
|---|---|
| ggtgcatcgt acgatgcagg gggg | 24 |

<210> SEQ ID NO 41
<211> LENGTH: 22
<212> TYPE: DNA
<213> ORGANISM: Artificial Sequence
<220> FEATURE:
<223> OTHER INFORMATION: synthetic deoxynucleotide

<400> SEQUENCE: 41

| | |
|---|---|
| ggtgcgatcg atcgcagggg gg | 22 |

<210> SEQ ID NO 42
<211> LENGTH: 22
<212> TYPE: DNA
<213> ORGANISM: Artificial Sequence
<220> FEATURE:
<223> OTHER INFORMATION: synthetic deoxynucleotide

<400> SEQUENCE: 42

| | |
|---|---|
| ggggggg tcg atcgatgggg gg | 22 |

<210> SEQ ID NO 43
<211> LENGTH: 22
<212> TYPE: DNA
<213> ORGANISM: Artificial Sequence
<220> FEATURE:
<223> OTHER INFORMATION: synthetic deoxynucleotide

<400> SEQUENCE: 43

| | |
|---|---|
| ggggtcgtcg aacgttgggg gg | 22 |

<210> SEQ ID NO 44
<211> LENGTH: 17
<212> TYPE: DNA
<213> ORGANISM: Artificial Sequence -continued

```
<220> FEATURE:
<223> OTHER INFORMATION: synthetic deoxynucleotide

<400> SEQUENCE: 44
tgtcgttcct tgtcgtt                                                    17

<210> SEQ ID NO 45
<211> LENGTH: 24
<212> TYPE: DNA
<213> ORGANISM: Artificial Sequence
<220> FEATURE:
<223> OTHER INFORMATION: synthetic deoxynucleotide

<400> SEQUENCE: 45
ttcgcttcgc ttttcgcttc gctt                                            24

<210> SEQ ID NO 46
<211> LENGTH: 26
<212> TYPE: DNA
<213> ORGANISM: Artificial Sequence
<220> FEATURE:
<223> OTHER INFORMATION: synthetic deoxynucleotide

<400> SEQUENCE: 46
accgccaagg agaagccgca ggaggg                                          26

<210> SEQ ID NO 47
<211> LENGTH: 19
<212> TYPE: DNA
<213> ORGANISM: Artificial Sequence
<220> FEATURE:
<223> OTHER INFORMATION: synthetic deoxynucleotide

<400> SEQUENCE: 47
tacaacggcg aggaatacc                                                  19

<210> SEQ ID NO 48
<211> LENGTH: 21
<212> TYPE: DNA
<213> ORGANISM: Artificial Sequence
<220> FEATURE:
<223> OTHER INFORMATION: synthetic deoxynucleotide

<400> SEQUENCE: 48
gtacaacggc gaggaatacc t                                               21

<210> SEQ ID NO 49
<211> LENGTH: 20
<212> TYPE: DNA
<213> ORGANISM: Artificial Sequence
<220> FEATURE:
<223> OTHER INFORMATION: synthetic deoxynucleotide

<400> SEQUENCE: 49
accgtcgttg ccgtcggccc                                                 20

<210> SEQ ID NO 50
<211> LENGTH: 14
<212> TYPE: DNA
<213> ORGANISM: Artificial Sequence
<220> FEATURE:
<223> OTHER INFORMATION: synthetic deoxynucleotide

<400> SEQUENCE: 50
tgctggccgt cgtt                                                       14
```

```
<210> SEQ ID NO 51
<211> LENGTH: 14
<212> TYPE: DNA
<213> ORGANISM: Artificial Sequence
<220> FEATURE:
<223> OTHER INFORMATION: synthetic deoxynucleotide

<400> SEQUENCE: 51
gtcggcacgc gacg                                                       14

<210> SEQ ID NO 52
<211> LENGTH: 20
<212> TYPE: DNA
<213> ORGANISM: Artificial Sequence
<220> FEATURE:
<223> OTHER INFORMATION: synthetic deoxynucleotide

<400> SEQUENCE: 52
gtcggcacgc gacgcccccc                                                 20

<210> SEQ ID NO 53
<211> LENGTH: 14
<212> TYPE: DNA
<213> ORGANISM: Artificial Sequence
<220> FEATURE:
<223> OTHER INFORMATION: synthetic deoxynucleotide

<400> SEQUENCE: 53
tcccgctgga cgtt                                                       14

<210> SEQ ID NO 54
<211> LENGTH: 23
<212> TYPE: DNA
<213> ORGANISM: Artificial Sequence
<220> FEATURE:
<223> OTHER INFORMATION: synthetic deoxynucleotide

<400> SEQUENCE: 54
ttaccggtta acgttggccg gcc                                             23

<210> SEQ ID NO 55
<211> LENGTH: 23
<212> TYPE: DNA
<213> ORGANISM: Artificial Sequence
<220> FEATURE:
<223> OTHER INFORMATION: synthetic deoxynucleotide

<400> SEQUENCE: 55
accggttaac gttgtccccg ggg                                             23

<210> SEQ ID NO 56
<211> LENGTH: 24
<212> TYPE: DNA
<213> ORGANISM: Artificial Sequence
<220> FEATURE:
<223> OTHER INFORMATION: synthetic deoxynucleotide

<400> SEQUENCE: 56
cgttgacgat cgtcccatgg cggg                                            24

<210> SEQ ID NO 57
<211> LENGTH: 16
<212> TYPE: DNA
<213> ORGANISM: Artificial Sequence
<220> FEATURE:
<223> OTHER INFORMATION: synthetic deoxynucleotide
```

```
<400> SEQUENCE: 57
tctgcggcct tcgtcg                                              16

<210> SEQ ID NO 58
<211> LENGTH: 22
<212> TYPE: DNA
<213> ORGANISM: Artificial Sequence
<220> FEATURE:
<223> OTHER INFORMATION: synthetic deoxynucleotide

<400> SEQUENCE: 58
tagtaaccgg tccggcgccc cc                                       22

<210> SEQ ID NO 59
<211> LENGTH: 19
<212> TYPE: DNA
<213> ORGANISM: Artificial Sequence
<220> FEATURE:
<223> OTHER INFORMATION: synthetic deoxynucleotide

<400> SEQUENCE: 59
ttgcagcgct gccggtggg                                           19

<210> SEQ ID NO 60
<211> LENGTH: 21
<212> TYPE: DNA
<213> ORGANISM: Artificial Sequence
<220> FEATURE:
<223> OTHER INFORMATION: synthetic deoxynucleotide

<400> SEQUENCE: 60
cggcccatcg agggcgacgg c                                        21

<210> SEQ ID NO 61
<211> LENGTH: 20
<212> TYPE: DNA
<213> ORGANISM: Artificial Sequence
<220> FEATURE:
<223> OTHER INFORMATION: synthetic deoxynucleotide

<400> SEQUENCE: 61
tcatcgactc tcgagcgttc                                          20

<210> SEQ ID NO 62
<211> LENGTH: 21
<212> TYPE: DNA
<213> ORGANISM: Artificial Sequence
<220> FEATURE:
<223> OTHER INFORMATION: synthetic deoxynucleotide

<400> SEQUENCE: 62
atcgtcgact ctcgtgttct c                                        21

<210> SEQ ID NO 63
<211> LENGTH: 23
<212> TYPE: DNA
<213> ORGANISM: Artificial Sequence
<220> FEATURE:
<223> OTHER INFORMATION: synthetic deoxynucleotide

<400> SEQUENCE: 63
tgcagcttgc tgcttgctgc ttc                                      23

<210> SEQ ID NO 64
```

```
<211> LENGTH: 20
<212> TYPE: DNA
<213> ORGANISM: Artificial Sequence
<220> FEATURE:
<223> OTHER INFORMATION: synthetic deoxynucleotide

<400> SEQUENCE: 64
ggtgcgacgt cgcagatgat                                                    20

<210> SEQ ID NO 65
<211> LENGTH: 20
<212> TYPE: DNA
<213> ORGANISM: Artificial Sequence
<220> FEATURE:
<223> OTHER INFORMATION: synthetic deoxynucleotide

<400> SEQUENCE: 65
ggtcgaacgt tcgagatgat                                                    20

<210> SEQ ID NO 66
<211> LENGTH: 26
<212> TYPE: DNA
<213> ORGANISM: Artificial Sequence
<220> FEATURE:
<223> OTHER INFORMATION: synthetic deoxynucleotide

<400> SEQUENCE: 66 ggggcgtcg ttttcgtcga cgaatt                                              26

<210> SEQ ID NO 67
<211> LENGTH: 24
<212> TYPE: DNA
<213> ORGANISM: Artificial Sequence
<220> FEATURE:
<223> OTHER INFORMATION: synthetic deoxynucleotide

<400> SEQUENCE: 67
actcgagacg cccgttgata gctt                                               24

<210> SEQ ID NO 68
<211> LENGTH: 24
<212> TYPE: DNA
<213> ORGANISM: Artificial Sequence
<220> FEATURE:
<223> OTHER INFORMATION: synthetic deoxynucleotide

<400> SEQUENCE: 68
aacgttggcg tcgacgtcag cgcc                                               24

<210> SEQ ID NO 69
<211> LENGTH: 18
<212> TYPE: DNA
<213> ORGANISM: Artificial Sequence
<220> FEATURE:
<223> OTHER INFORMATION: synthetic deoxynucleotide

<400> SEQUENCE: 69
gacgtcgacg ttgacgct                                                      18

<210> SEQ ID NO 70
<211> LENGTH: 18
<212> TYPE: DNA
<213> ORGANISM: Artificial Sequence
<220> FEATURE:
<223> OTHER INFORMATION: synthetic deoxynucleotide

<400> SEQUENCE: 70
```

```
ggcgttaacg ttagcgct                                              18

<210> SEQ ID NO 71
<211> LENGTH: 18
<212> TYPE: DNA
<213> ORGANISM: Artificial Sequence
<220> FEATURE:
<223> OTHER INFORMATION: synthetic deoxynucleotide

<400> SEQUENCE: 71
agcgctagcg ctgacgtt                                              18

<210> SEQ ID NO 72
<211> LENGTH: 17
<212> TYPE: DNA
<213> ORGANISM: Artificial Sequence
<220> FEATURE:
<223> OTHER INFORMATION: synthetic deoxynucleotide

<400> SEQUENCE: 72
ctagacgttc aagcgtt                                               17

<210> SEQ ID NO 73
<211> LENGTH: 20
<212> TYPE: DNA
<213> ORGANISM: Artificial Sequence
<220> FEATURE:
<223> OTHER INFORMATION: synthetic deoxynucleotide

<400> SEQUENCE: 73
gacgatcgtc gacgatcgtc                                            20

<210> SEQ ID NO 74
<211> LENGTH: 24
<212> TYPE: DNA
<213> ORGANISM: Artificial Sequence
<220> FEATURE:
<223> OTHER INFORMATION: synthetic deoxynucleotide

<400> SEQUENCE: 74
gtcgttcgta gtcgactacg agtt                                       24

<210> SEQ ID NO 75
<211> LENGTH: 26
<212> TYPE: DNA
<213> ORGANISM: Artificial Sequence
<220> FEATURE:
<223> OTHER INFORMATION: synthetic deoxynucleotide

<400> SEQUENCE: 75
aaaagacgtc gacgtcgacg tctttt                                     26

<210> SEQ ID NO 76
<211> LENGTH: 25
<212> TYPE: DNA
<213> ORGANISM: Artificial Sequence
<220> FEATURE:
<223> OTHER INFORMATION: synthetic deoxynucleotide

<400> SEQUENCE: 76
tgcgacgatc gtcgcacgat cggat                                      25

<210> SEQ ID NO 77
<211> LENGTH: 18
<212> TYPE: DNA
```

```
<213> ORGANISM: Artificial Sequence
<220> FEATURE:
<223> OTHER INFORMATION: synthetic deoxynucleotide

<400> SEQUENCE: 77
tgcgacgtcg cacagcgt                                                 18

<210> SEQ ID NO 78
<211> LENGTH: 13
<212> TYPE: DNA
<213> ORGANISM: Artificial Sequence
<220> FEATURE:
<223> OTHER INFORMATION: synthetic deoxynucleotide

<400> SEQUENCE: 78
tcgttgccgt cgg                                                      13

<210> SEQ ID NO 79
<211> LENGTH: 14
<212> TYPE: DNA
<213> ORGANISM: Artificial Sequence
<220> FEATURE:
<223> OTHER INFORMATION: synthetic deoxynucleotide

<400> SEQUENCE: 79
tcgttgccgt cggg                                                     14

<210> SEQ ID NO 80
<211> LENGTH: 15
<212> TYPE: DNA
<213> ORGANISM: Artificial Sequence
<220> FEATURE:
<223> OTHER INFORMATION: synthetic deoxynucleotide

<400> SEQUENCE: 80
tcgttgccgt cgggg                                                    15

<210> SEQ ID NO 81
<211> LENGTH: 16
<212> TYPE: DNA
<213> ORGANISM: Artificial Sequence
<220> FEATURE:
<223> OTHER INFORMATION: synthetic deoxynucleotide

<400> SEQUENCE: 81
tcgttgccgt cggggg                                                   16

<210> SEQ ID NO 82
<211> LENGTH: 17
<212> TYPE: DNA
<213> ORGANISM: Artificial Sequence
<220> FEATURE:
<223> OTHER INFORMATION: synthetic deoxynucleotide

<400> SEQUENCE: 82
tcgttgccgt cgggggg                                                  17

<210> SEQ ID NO 83
<211> LENGTH: 18
<212> TYPE: DNA
<213> ORGANISM: Artificial Sequence
<220> FEATURE:
<223> OTHER INFORMATION: synthetic deoxynucleotide

<400> SEQUENCE: 83
tcgttgccgt cggggggg                                                 18
```

```
<210> SEQ ID NO 84
<211> LENGTH: 19
<212> TYPE: DNA
<213> ORGANISM: Artificial Sequence
<220> FEATURE:
<223> OTHER INFORMATION: synthetic deoxynucleotide

<400> SEQUENCE: 84
tcgttgccgt cggggggg                                             19

<210> SEQ ID NO 85
<211> LENGTH: 20
<212> TYPE: DNA
<213> ORGANISM: Artificial Sequence
<220> FEATURE:
<223> OTHER INFORMATION: synthetic deoxynucleotide

<400> SEQUENCE: 85
tcgttgccgt cggggggggg                                           20

<210> SEQ ID NO 86
<211> LENGTH: 26
<212> TYPE: DNA
<213> ORGANISM: Artificial Sequence
<220> FEATURE:
<223> OTHER INFORMATION: synthetic deoxynucleotide

<400> SEQUENCE: 86
tcgtcgggtg catcgatgca gggggg                                    26

<210> SEQ ID NO 87
<211> LENGTH: 26
<212> TYPE: DNA
<213> ORGANISM: Artificial Sequence
<220> FEATURE:
<223> OTHER INFORMATION: synthetic deoxynucleotide

<400> SEQUENCE: 87
tcgtcgggtg caacgttgca gggggg                                    26

<210> SEQ ID NO 88
<211> LENGTH: 26
<212> TYPE: DNA
<213> ORGANISM: Artificial Sequence
<220> FEATURE:
<223> OTHER INFORMATION: synthetic deoxynucleotide

<400> SEQUENCE: 88
tcgtcgggtg cgtcgacgca gggggg                                    26

<210> SEQ ID NO 89
<211> LENGTH: 24
<212> TYPE: DNA
<213> ORGANISM: Artificial Sequence
<220> FEATURE:
<223> OTHER INFORMATION: synthetic deoxynucleotide

<400> SEQUENCE: 89
tcgtcgggtg cgatcgcagg gggg                                      24

<210> SEQ ID NO 90
<211> LENGTH: 30
<212> TYPE: DNA
<213> ORGANISM: Artificial Sequence
<220> FEATURE:
```

<223> OTHER INFORMATION: synthetic deoxynucleotide

<400> SEQUENCE: 90
tcgtcgggtg cgacgatcgt cgcagggggg                30

<210> SEQ ID NO 91
<211> LENGTH: 24
<212> TYPE: DNA
<213> ORGANISM: Artificial Sequence
<220> FEATURE:
<223> OTHER INFORMATION: synthetic deoxynucleotide

<400> SEQUENCE: 91
tcgtcgtgcg acgtcgcagg gggg                24

<210> SEQ ID NO 92
<211> LENGTH: 23
<212> TYPE: DNA
<213> ORGANISM: Artificial Sequence
<220> FEATURE:
<223> OTHER INFORMATION: synthetic deoxynucleotide

<400> SEQUENCE: 92
tcgtcgcaga acgttctggg ggg                23

<210> SEQ ID NO 93
<211> LENGTH: 21
<212> TYPE: DNA
<213> ORGANISM: Artificial Sequence
<220> FEATURE:
<223> OTHER INFORMATION: synthetic deoxynucleotide

<400> SEQUENCE: 93
tcgtgcgacg tcgcaggggg g                21

<210> SEQ ID NO 94
<211> LENGTH: 25
<212> TYPE: DNA
<213> ORGANISM: Artificial Sequence
<220> FEATURE:
<223> OTHER INFORMATION: synthetic deoxynucleotide

<400> SEQUENCE: 94
tcgtgcgacg atcgtcgcag ggggg                25

<210> SEQ ID NO 95
<211> LENGTH: 25
<212> TYPE: DNA
<213> ORGANISM: Artificial Sequence
<220> FEATURE:
<223> OTHER INFORMATION: synthetic deoxynucleotide

<400> SEQUENCE: 95
tcgtatgcat cgatgcatag ggagg                25

<210> SEQ ID NO 96
<211> LENGTH: 21
<212> TYPE: DNA
<213> ORGANISM: Artificial Sequence
<220> FEATURE:
<223> OTHER INFORMATION: synthetic deoxynucleotide

<400> SEQUENCE: 96
tcgtgcatcg atgcaggggg g                21

<210> SEQ ID NO 97
<211> LENGTH: 18
<212> TYPE: DNA
<213> ORGANISM: Artificial Sequence
<220> FEATURE:
<223> OTHER INFORMATION: synthetic deoxynucleotide

<400> SEQUENCE: 97
tcgaaacgtt tcgggggg                                              18

<210> SEQ ID NO 98
<211> LENGTH: 19
<212> TYPE: DNA
<213> ORGANISM: Artificial Sequence
<220> FEATURE:
<223> OTHER INFORMATION: synthetic deoxynucleotide

<400> SEQUENCE: 98
tcggacgatc gtcggggggg                                            19

<210> SEQ ID NO 99
<211> LENGTH: 22
<212> TYPE: DNA
<213> ORGANISM: Artificial Sequence
<220> FEATURE:
<223> OTHER INFORMATION: synthetic deoxynucleotide

<400> SEQUENCE: 99
tcgagcgatc gctcgagggg gg                                         22

<210> SEQ ID NO 100
<211> LENGTH: 20
<212> TYPE: DNA
<213> ORGANISM: Artificial Sequence
<220> FEATURE:
<223> OTHER INFORMATION: synthetic deoxynucleotide

<400> SEQUENCE: 100
tcgtcgcttt gtcgttgggg                                            20

<210> SEQ ID NO 101
<211> LENGTH: 20
<212> TYPE: DNA
<213> ORGANISM: Artificial Sequence
<220> FEATURE:
<223> OTHER INFORMATION: synthetic deoxynucleotide

<400> SEQUENCE: 101
tcgtcgtttt gtcgttgggg                                            20

<210> SEQ ID NO 102
<211> LENGTH: 26
<212> TYPE: DNA
<213> ORGANISM: Artificial Sequence
<220> FEATURE:
<223> OTHER INFORMATION: synthetic deoxynucleotide

<400> SEQUENCE: 102
tcgtcgggtg cgacgtcgca gggggg                                     26

<210> SEQ ID NO 103
<211> LENGTH: 27
<212> TYPE: DNA
<213> ORGANISM: Artificial Sequence
<220> FEATURE:
<223> OTHER INFORMATION: synthetic deoxynucleotide

<400> SEQUENCE: 103
tcgtcgggtg cgacgatcgt cgggggg         27

<210> SEQ ID NO 104
<211> LENGTH: 27
<212> TYPE: DNA
<213> ORGANISM: Artificial Sequence
<220> FEATURE:
<223> OTHER INFORMATION: synthetic deoxynucleotide

<400> SEQUENCE: 104
tcgtcgtttg catcgatgca ggggggg         27

<210> SEQ ID NO 105
<211> LENGTH: 26
<212> TYPE: DNA
<213> ORGANISM: Artificial Sequence
<220> FEATURE:
<223> OTHER INFORMATION: synthetic deoxynucleotide

<400> SEQUENCE: 105
tcgtcgtttt gacgatcgtc gggggg         26

<210> SEQ ID NO 106
<211> LENGTH: 15
<212> TYPE: DNA
<213> ORGANISM: Artificial Sequence
<220> FEATURE:
<223> OTHER INFORMATION: synthetic deoxynucleotide

<400> SEQUENCE: 106
tcgttcgggg tgccg         15

<210> SEQ ID NO 107
<211> LENGTH: 21
<212> TYPE: DNA
<213> ORGANISM: Artificial Sequence
<220> FEATURE:
<223> OTHER INFORMATION: synthetic deoxynucleotide

<400> SEQUENCE: 107
tcgttcgggg taccgatggg g         21

<210> SEQ ID NO 108
<211> LENGTH: 24
<212> TYPE: DNA
<213> ORGANISM: Artificial Sequence
<220> FEATURE:
<223> OTHER INFORMATION: synthetic deoxynucleotide

<400> SEQUENCE: 108
tcgttgcgct cccatgccgg gggg         24

<210> SEQ ID NO 109
<211> LENGTH: 20
<212> TYPE: DNA
<213> ORGANISM: Artificial Sequence
<220> FEATURE:
<223> OTHER INFORMATION: synthetic deoxynucleotide

<400> SEQUENCE: 109
tcgtcgtttc gtcgttgggg         20

<210> SEQ ID NO 110
<211> LENGTH: 27

```
<212> TYPE: DNA
<213> ORGANISM: Artificial Sequence
<220> FEATURE:
<223> OTHER INFORMATION: synthetic deoxynucleotide

<400> SEQUENCE: 110
tcgttgtcgt ttcgctgccg gcggggg                                        27

<210> SEQ ID NO 111
<211> LENGTH: 26
<212> TYPE: DNA
<213> ORGANISM: Artificial Sequence
<220> FEATURE:
<223> OTHER INFORMATION: synthetic deoxynucleotide

<400> SEQUENCE: 111
tgcttgggtg gcagctgcca gggggg                                         26

<210> SEQ ID NO 112
<211> LENGTH: 20
<212> TYPE: DNA
<213> ORGANISM: Artificial Sequence
<220> FEATURE:
<223> OTHER INFORMATION: synthetic deoxynucleotide

<400> SEQUENCE: 112
tgctgctttg ctgcttgggg                                                20

<210> SEQ ID NO 113
<211> LENGTH: 24
<212> TYPE: DNA
<213> ORGANISM: Artificial Sequence
<220> FEATURE:
<223> OTHER INFORMATION: synthetic deoxynucleotide

<400> SEQUENCE: 113
aacgttcgac gtcgaacggg gggg                                           24

<210> SEQ ID NO 114
<211> LENGTH: 17
<212> TYPE: DNA
<213> ORGANISM: Artificial Sequence
<220> FEATURE:
<223> OTHER INFORMATION: synthetic deoxynucleotide

<400> SEQUENCE: 114
aacgacgacg ttggggg                                                   17

<210> SEQ ID NO 115
<211> LENGTH: 22
<212> TYPE: DNA
<213> ORGANISM: Artificial Sequence
<220> FEATURE:
<223> OTHER INFORMATION: synthetic deoxynucleotide

<400> SEQUENCE: 115
tcgtaacgtt gttttttaacg tt                                            22

<210> SEQ ID NO 116
<211> LENGTH: 21
<212> TYPE: DNA
<213> ORGANISM: Artificial Sequence
<220> FEATURE:
<223> OTHER INFORMATION: synthetic deoxynucleotide

<400> SEQUENCE: 116
```
tcgtcgtata cgacgatcgt t					21

<210> SEQ ID NO 117
<211> LENGTH: 20
<212> TYPE: DNA
<213> ORGANISM: Artificial Sequence
<220> FEATURE:
<223> OTHER INFORMATION: synthetic deoxynucleotide

<400> SEQUENCE: 117
tcgtcgtttg cgttgtcgtt					20

<210> SEQ ID NO 118
<211> LENGTH: 18
<212> TYPE: DNA
<213> ORGANISM: Artificial Sequence
<220> FEATURE:
<223> OTHER INFORMATION: synthetic deoxynucleotide

<400> SEQUENCE: 118
tcctgtcgtt ttgtcgtt					18

<210> SEQ ID NO 119
<211> LENGTH: 18
<212> TYPE: DNA
<213> ORGANISM: Artificial Sequence
<220> FEATURE:
<223> OTHER INFORMATION: synthetic deoxynucleotide

<400> SEQUENCE: 119
tcgtcgttgt cgttcgct					18

<210> SEQ ID NO 120
<211> LENGTH: 25
<212> TYPE: DNA
<213> ORGANISM: Artificial Sequence
<220> FEATURE:
<223> OTHER INFORMATION: synthetic deoxynucleotide

<400> SEQUENCE: 120
tcgtcgttac cgatgacgtc gccgt					25

<210> SEQ ID NO 121
<211> LENGTH: 29
<212> TYPE: DNA
<213> ORGANISM: Artificial Sequence
<220> FEATURE:
<223> OTHER INFORMATION: synthetic deoxynucleotide

<400> SEQUENCE: 121
tcgtcgtttg catcgatgca gtcgtcgtt					29

<210> SEQ ID NO 122
<211> LENGTH: 21
<212> TYPE: DNA
<213> ORGANISM: Artificial Sequence
<220> FEATURE:
<223> OTHER INFORMATION: synthetic deoxynucleotide

<400> SEQUENCE: 122
tcgcctcgtc gccttcgagc g					21

<210> SEQ ID NO 123
<211> LENGTH: 20
<212> TYPE: DNA
<213> ORGANISM: Artificial Sequence

```
<220> FEATURE:
<223> OTHER INFORMATION: synthetic deoxynucleotide

<400> SEQUENCE: 123
tcgtgtgcgt gccgttgggt                                              20

<210> SEQ ID NO 124
<211> LENGTH: 20
<212> TYPE: DNA
<213> ORGANISM: Artificial Sequence
<220> FEATURE:
<223> OTHER INFORMATION: synthetic deoxynucleotide

<400> SEQUENCE: 124
tcgtcgaggg cgccggtgac                                              20

<210> SEQ ID NO 125
<211> LENGTH: 20
<212> TYPE: DNA
<213> ORGANISM: Artificial Sequence
<220> FEATURE:
<223> OTHER INFORMATION: synthetic deoxynucleotide

<400> SEQUENCE: 125
tcgtcgccgg tgggggtgtg                                              20

<210> SEQ ID NO 126
<211> LENGTH: 20
<212> TYPE: DNA
<213> ORGANISM: Artificial Sequence
<220> FEATURE:
<223> OTHER INFORMATION: synthetic deoxynucleotide

<400> SEQUENCE: 126
tcgtcgtacg caattgtctt                                              20

<210> SEQ ID NO 127
<211> LENGTH: 20
<212> TYPE: DNA
<213> ORGANISM: Artificial Sequence
<220> FEATURE:
<223> OTHER INFORMATION: synthetic deoxynucleotide

<400> SEQUENCE: 127
tcgcccaccg gtggggggg                                               20

<210> SEQ ID NO 128
<211> LENGTH: 21
<212> TYPE: DNA
<213> ORGANISM: Artificial Sequence
<220> FEATURE:
<223> OTHER INFORMATION: synthetic deoxynucleotide

<400> SEQUENCE: 128
tcgtcgcaga ccggtctggg g                                            21

<210> SEQ ID NO 129
<211> LENGTH: 20
<212> TYPE: DNA
<213> ORGANISM: Artificial Sequence
<220> FEATURE:
<223> OTHER INFORMATION: synthetic deoxynucleotide

<400> SEQUENCE: 129
tcgtcgcggc cggcgccccc                                              20
```

<210> SEQ ID NO 130
<211> LENGTH: 20
<212> TYPE: DNA
<213> ORGANISM: Artificial Sequence
<220> FEATURE:
<223> OTHER INFORMATION: synthetic deoxynucleotide

<400> SEQUENCE: 130
tcgtcgcggc cgcgaggggg                                           20

<210> SEQ ID NO 131
<211> LENGTH: 21
<212> TYPE: DNA
<213> ORGANISM: Artificial Sequence
<220> FEATURE:
<223> OTHER INFORMATION: synthetic deoxynucleotide

<400> SEQUENCE: 131
tcgaggacaa gattctcgtg c                                         21

<210> SEQ ID NO 132
<211> LENGTH: 26
<212> TYPE: DNA
<213> ORGANISM: Artificial Sequence
<220> FEATURE:
<223> OTHER INFORMATION: synthetic deoxynucleotide

<400> SEQUENCE: 132
tcgaggacaa gattctcgtg caggcc                                    26

<210> SEQ ID NO 133
<211> LENGTH: 21
<212> TYPE: DNA
<213> ORGANISM: Artificial Sequence
<220> FEATURE:
<223> OTHER INFORMATION: synthetic deoxynucleotide

<400> SEQUENCE: 133
tcgtgcaggc caacgaggcc g                                         21

<210> SEQ ID NO 134
<211> LENGTH: 16
<212> TYPE: DNA
<213> ORGANISM: Artificial Sequence
<220> FEATURE:
<223> OTHER INFORMATION: synthetic deoxynucleotide

<400> SEQUENCE: 134
tcgttgccgt cggccc                                               16

<210> SEQ ID NO 135
<211> LENGTH: 30
<212> TYPE: DNA
<213> ORGANISM: Artificial Sequence
<220> FEATURE:
<223> OTHER INFORMATION: synthetic deoxynucleotide

<400> SEQUENCE: 135
tcggcacgcg acgtgctggc cgtcgtttcc                                30

<210> SEQ ID NO 136
<211> LENGTH: 22
<212> TYPE: DNA
<213> ORGANISM: Artificial Sequence
<220> FEATURE:
<223> OTHER INFORMATION: synthetic deoxynucleotide

```
<400> SEQUENCE: 136
tcgttgccgt cggcccccc cc                                    22

<210> SEQ ID NO 137
<211> LENGTH: 19
<212> TYPE: DNA
<213> ORGANISM: Artificial Sequence
<220> FEATURE:
<223> OTHER INFORMATION: synthetic deoxynucleotide

<400> SEQUENCE: 137
tcgttgccgt cggcccccc                                       19

<210> SEQ ID NO 138
<211> LENGTH: 18
<212> TYPE: DNA
<213> ORGANISM: Artificial Sequence
<220> FEATURE:
<223> OTHER INFORMATION: synthetic deoxynucleotide

<400> SEQUENCE: 138
tcgttgccgt cggccccc                                        18

<210> SEQ ID NO 139
<211> LENGTH: 17
<212> TYPE: DNA
<213> ORGANISM: Artificial Sequence
<220> FEATURE:
<223> OTHER INFORMATION: synthetic deoxynucleotide

<400> SEQUENCE: 139
tcgttgccgt cggcccc                                         17

<210> SEQ ID NO 140
<211> LENGTH: 20
<212> TYPE: DNA
<213> ORGANISM: Artificial Sequence
<220> FEATURE:
<223> OTHER INFORMATION: synthetic deoxynucleotide

<400> SEQUENCE: 140
tcgttgccgt cggccccccc                                      20

<210> SEQ ID NO 141
<211> LENGTH: 19
<212> TYPE: DNA
<213> ORGANISM: Artificial Sequence
<220> FEATURE:
<223> OTHER INFORMATION: synthetic deoxynucleotide

<400> SEQUENCE: 141
tcgaggacaa gattctcgt                                       19

<210> SEQ ID NO 142
<211> LENGTH: 27
<212> TYPE: DNA
<213> ORGANISM: Artificial Sequence
<220> FEATURE:
<223> OTHER INFORMATION: synthetic deoxynucleotide

<400> SEQUENCE: 142
tcggcacgcg acgtgctggc cgtcgtt                              27

<210> SEQ ID NO 143
```

<211> LENGTH: 21
<212> TYPE: DNA
<213> ORGANISM: Artificial Sequence
<220> FEATURE:
<223> OTHER INFORMATION: synthetic deoxynucleotide

<400> SEQUENCE: 143
tcgtcgcgcc gtcacgggggg g                                          21

<210> SEQ ID NO 144
<211> LENGTH: 19
<212> TYPE: DNA
<213> ORGANISM: Artificial Sequence
<220> FEATURE:
<223> OTHER INFORMATION: synthetic deoxynucleotide

<400> SEQUENCE: 144
tcgtgtgcgt gccgttggg                                              19

<210> SEQ ID NO 145
<211> LENGTH: 18
<212> TYPE: DNA
<213> ORGANISM: Artificial Sequence
<220> FEATURE:
<223> OTHER INFORMATION: synthetic deoxynucleotide

<400> SEQUENCE: 145
tcgtcgccgt tgggcggg                                               18

<210> SEQ ID NO 146
<211> LENGTH: 21
<212> TYPE: DNA
<213> ORGANISM: Artificial Sequence
<220> FEATURE:
<223> OTHER INFORMATION: synthetic deoxynucleotide

<400> SEQUENCE: 146
tcgtcgacgt cgttgggcgg g                                           21

<210> SEQ ID NO 147
<211> LENGTH: 26
<212> TYPE: DNA
<213> ORGANISM: Artificial Sequence
<220> FEATURE:
<223> OTHER INFORMATION: synthetic deoxynucleotide

<400> SEQUENCE: 147
tcgcagttgt cgtaacgttg ggcggg                                      26

<210> SEQ ID NO 148
<211> LENGTH: 16
<212> TYPE: DNA
<213> ORGANISM: Artificial Sequence
<220> FEATURE:
<223> OTHER INFORMATION: synthetic deoxynucleotide

<400> SEQUENCE: 148
tcgtcgttgg tatgtt                                                 16

<210> SEQ ID NO 149
<211> LENGTH: 20
<212> TYPE: DNA
<213> ORGANISM: Artificial Sequence
<220> FEATURE:
<223> OTHER INFORMATION: synthetic deoxynucleotide

<400> SEQUENCE: 149
tcgtcgtcgt cgttgtcgtt                                              20

<210> SEQ ID NO 150
<211> LENGTH: 24
<212> TYPE: DNA
<213> ORGANISM: Artificial Sequence
<220> FEATURE:
<223> OTHER INFORMATION: synthetic deoxynucleotide

<400> SEQUENCE: 150
tcgtcgtcgt cgttgtcgtt gggg                                         24

<210> SEQ ID NO 151
<211> LENGTH: 15
<212> TYPE: DNA
<213> ORGANISM: Artificial Sequence
<220> FEATURE:
<223> OTHER INFORMATION: synthetic deoxynucleotide

<400> SEQUENCE: 151
tcgttcgggg tgccg                                                   15

<210> SEQ ID NO 152
<211> LENGTH: 18
<212> TYPE: DNA
<213> ORGANISM: Artificial Sequence
<220> FEATURE:
<223> OTHER INFORMATION: synthetic deoxynucleotide

<400> SEQUENCE: 152
tcgttcgggg taacgatt                                                18

<210> SEQ ID NO 153
<211> LENGTH: 17
<212> TYPE: DNA
<213> ORGANISM: Artificial Sequence
<220> FEATURE:
<223> OTHER INFORMATION: synthetic deoxynucleotide

<400> SEQUENCE: 153
tcgttcgggg taacgtt                                                 17

<210> SEQ ID NO 154
<211> LENGTH: 17
<212> TYPE: DNA
<213> ORGANISM: Artificial Sequence
<220> FEATURE:
<223> OTHER INFORMATION: synthetic deoxynucleotide

<400> SEQUENCE: 154
tcgttcgggg taccgat                                                 17

<210> SEQ ID NO 155
<211> LENGTH: 23
<212> TYPE: DNA
<213> ORGANISM: Artificial Sequence
<220> FEATURE:
<223> OTHER INFORMATION: synthetic deoxynucleotide

<400> SEQUENCE: 155
tcgtacggcc gccgtacggc ggg                                          23

<210> SEQ ID NO 156
<211> LENGTH: 23
<212> TYPE: DNA

```
<213> ORGANISM: Artificial Sequence
<220> FEATURE:
<223> OTHER INFORMATION: synthetic deoxynucleotide

<400> SEQUENCE: 156
tcgcgtcgac tcccctcgag ggg                                           23

<210> SEQ ID NO 157
<211> LENGTH: 24
<212> TYPE: DNA
<213> ORGANISM: Artificial Sequence
<220> FEATURE:
<223> OTHER INFORMATION: synthetic deoxynucleotide

<400> SEQUENCE: 157
tcgtcgtcga ctcgtggtcg gggg                                          24

<210> SEQ ID NO 158
<211> LENGTH: 20
<212> TYPE: DNA
<213> ORGANISM: Artificial Sequence
<220> FEATURE:
<223> OTHER INFORMATION: synthetic deoxynucleotide

<400> SEQUENCE: 158
tcgggcgccc gatcggggggg                                              20

<210> SEQ ID NO 159
<211> LENGTH: 19
<212> TYPE: DNA
<213> ORGANISM: Artificial Sequence
<220> FEATURE:
<223> OTHER INFORMATION: synthetic deoxynucleotide

<400> SEQUENCE: 159
tcgtcggtct ttcgaaatt                                                19

<210> SEQ ID NO 160
<211> LENGTH: 18
<212> TYPE: DNA
<213> ORGANISM: Artificial Sequence
<220> FEATURE:
<223> OTHER INFORMATION: synthetic deoxynucleotide

<400> SEQUENCE: 160
tcgtgacgtc ctcgagtt                                                 18

<210> SEQ ID NO 161
<211> LENGTH: 20
<212> TYPE: DNA
<213> ORGANISM: Artificial Sequence
<220> FEATURE:
<223> OTHER INFORMATION: synthetic deoxynucleotide

<400> SEQUENCE: 161
tcgtctttcg actcgttctc                                               20

<210> SEQ ID NO 162
<211> LENGTH: 18
<212> TYPE: DNA
<213> ORGANISM: Artificial Sequence
<220> FEATURE:
<223> OTHER INFORMATION: synthetic deoxynucleotide

<400> SEQUENCE: 162
tcgtcgtttt gcgttctc                                                 18
```

<210> SEQ ID NO 163
<211> LENGTH: 20
<212> TYPE: DNA
<213> ORGANISM: Artificial Sequence
<220> FEATURE:
<223> OTHER INFORMATION: synthetic deoxynucleotide

<400> SEQUENCE: 163
tcgactttcg tcgttctgtt                                              20

<210> SEQ ID NO 164
<211> LENGTH: 19
<212> TYPE: DNA
<213> ORGANISM: Artificial Sequence
<220> FEATURE:
<223> OTHER INFORMATION: synthetic deoxynucleotide

<400> SEQUENCE: 164
tcgtcgtttc gtcgttctc                                               19

<210> SEQ ID NO 165
<211> LENGTH: 20
<212> TYPE: DNA
<213> ORGANISM: Artificial Sequence
<220> FEATURE:
<223> OTHER INFORMATION: synthetic deoxynucleotide

<400> SEQUENCE: 165
tcgtcgtcgt cgttgtcgtt                                              20

<210> SEQ ID NO 166
<211> LENGTH: 19
<212> TYPE: DNA
<213> ORGANISM: Artificial Sequence
<220> FEATURE:
<223> OTHER INFORMATION: synthetic deoxynucleotide

<400> SEQUENCE: 166
tcgttctcga ctcgttctc                                               19

<210> SEQ ID NO 167
<211> LENGTH: 23
<212> TYPE: DNA
<213> ORGANISM: Artificial Sequence
<220> FEATURE:
<223> OTHER INFORMATION: synthetic deoxynucleotide

<400> SEQUENCE: 167
tcgacgttcg tcgttcgtcg ttc                                          23

<210> SEQ ID NO 168
<211> LENGTH: 21
<212> TYPE: DNA
<213> ORGANISM: Artificial Sequence
<220> FEATURE:
<223> OTHER INFORMATION: synthetic deoxynucleotide

<400> SEQUENCE: 168
tcgtcgacgt cgttcgttct c                                            21

<210> SEQ ID NO 169
<211> LENGTH: 21
<212> TYPE: DNA
<213> ORGANISM: Artificial Sequence
<220> FEATURE:

<223> OTHER INFORMATION: synthetic deoxynucleotide

<400> SEQUENCE: 169
tcgtgcgacg tcgcagatga t        21

<210> SEQ ID NO 170
<211> LENGTH: 21
<212> TYPE: DNA
<213> ORGANISM: Artificial Sequence
<220> FEATURE:
<223> OTHER INFORMATION: synthetic deoxynucleotide

<400> SEQUENCE: 170
tcgtcgagcg ctcgatcgga t        21

<210> SEQ ID NO 171
<211> LENGTH: 28
<212> TYPE: DNA
<213> ORGANISM: Artificial Sequence
<220> FEATURE:
<223> OTHER INFORMATION: synthetic deoxynucleotide

<400> SEQUENCE: 171
tcgtcgtttc gtagtcgttg acgtcggg        28

<210> SEQ ID NO 172
<211> LENGTH: 24
<212> TYPE: DNA
<213> ORGANISM: Artificial Sequence
<220> FEATURE:
<223> OTHER INFORMATION: synthetic deoxynucleotide

<400> SEQUENCE: 172
tcgtcggacg ttttccgacg ttct        24

<210> SEQ ID NO 173
<211> LENGTH: 26
<212> TYPE: DNA
<213> ORGANISM: Artificial Sequence
<220> FEATURE:
<223> OTHER INFORMATION: synthetic deoxynucleotide

<400> SEQUENCE: 173
tcgtcgtttt cgtcgttttc gtcgtt        26

<210> SEQ ID NO 174
<211> LENGTH: 22
<212> TYPE: DNA
<213> ORGANISM: Artificial Sequence
<220> FEATURE:
<223> OTHER INFORMATION: synthetic deoxynucleotide

<400> SEQUENCE: 174
tcgtcgtttg tcgtgtgtcg tt        22

<210> SEQ ID NO 175
<211> LENGTH: 30
<212> TYPE: DNA
<213> ORGANISM: Artificial Sequence
<220> FEATURE:
<223> OTHER INFORMATION: synthetic deoxynucleotide

<400> SEQUENCE: 175
tcgtcgttgg tcggggtcgt tggggtcgtt        30

<210> SEQ ID NO 176
<211> LENGTH: 20
<212> TYPE: DNA
<213> ORGANISM: Artificial Sequence
<220> FEATURE:
<223> OTHER INFORMATION: synthetic deoxynucleotide

<400> SEQUENCE: 176
tcgtcgtttc gtctctcgtt                                         20

<210> SEQ ID NO 177
<211> LENGTH: 21
<212> TYPE: DNA
<213> ORGANISM: Artificial Sequence
<220> FEATURE:
<223> OTHER INFORMATION: synthetic deoxynucleotide

<400> SEQUENCE: 177
tcgtcgtttt gctgcgtcgt t                                       21

<210> SEQ ID NO 178
<211> LENGTH: 21
<212> TYPE: DNA
<213> ORGANISM: Artificial Sequence
<220> FEATURE:
<223> OTHER INFORMATION: synthetic deoxynucleotide

<400> SEQUENCE: 178
tcgagcgttt tcgctcgaat t                                       21

<210> SEQ ID NO 179
<211> LENGTH: 30
<212> TYPE: DNA
<213> ORGANISM: Artificial Sequence
<220> FEATURE:
<223> OTHER INFORMATION: synthetic deoxynucleotide

<400> SEQUENCE: 179
ttcgtcgttt gatcgatgtt cgttgggggg                              30

<210> SEQ ID NO 180
<211> LENGTH: 24
<212> TYPE: DNA
<213> ORGANISM: Artificial Sequence
<220> FEATURE:
<223> OTHER INFORMATION: synthetic deoxynucleotide

<400> SEQUENCE: 180
ttcgtcgttg tgatcgatgg gggg                                    24

<210> SEQ ID NO 181
<211> LENGTH: 28
<212> TYPE: DNA
<213> ORGANISM: Artificial Sequence
<220> FEATURE:
<223> OTHER INFORMATION: synthetic deoxynucleotide

<400> SEQUENCE: 181
tatcgatgtt ttcgtcgtcg ttgggggg                                28

<210> SEQ ID NO 182
<211> LENGTH: 20
<212> TYPE: DNA
<213> ORGANISM: Artificial Sequence
<220> FEATURE:
<223> OTHER INFORMATION: synthetic deoxynucleotide

```
<400> SEQUENCE: 182
tcgactttcg tcgttctgtt                                               20

<210> SEQ ID NO 183
<211> LENGTH: 19
<212> TYPE: DNA
<213> ORGANISM: Artificial Sequence
<220> FEATURE:
<223> OTHER INFORMATION: synthetic deoxynucleotide

<400> SEQUENCE: 183
tcgtcgtttc gtcgttctc                                                19

<210> SEQ ID NO 184
<211> LENGTH: 23
<212> TYPE: DNA
<213> ORGANISM: Artificial Sequence
<220> FEATURE:
<223> OTHER INFORMATION: synthetic deoxynucleotide

<400> SEQUENCE: 184
tcgacgttcg tcgttcgtcg ttc                                           23

<210> SEQ ID NO 185
<211> LENGTH: 26
<212> TYPE: DNA
<213> ORGANISM: Artificial Sequence
<220> FEATURE:
<223> OTHER INFORMATION: synthetic deoxynucleotide

<400> SEQUENCE: 185
tcgtcgtttt cgtcgttttc gtcgtt                                        26
```